United States Patent
Starkweather et al.

(10) Patent No.: US 7,171,274 B2
(45) Date of Patent: *Jan. 30, 2007

(54) METHOD AND APPARATUS FOR COMMUNICATING BETWEEN AN AMBULATORY MEDICAL DEVICE AND A CONTROL DEVICE VIA TELEMETRY USING RANDOMIZED DATA

(75) Inventors: Timothy J. Starkweather, Simi Valley, CA (US); Ronald J. Lebel, Sherman Oaks, CA (US); Daniel H. Villegas, Granada Hills, CA (US); Philip T. Weiss, Pasadena, CA (US); John T. Armstrong, Pasadena, CA (US); John D. Richert, La Habra Heights, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 620 days.

This patent is subject to a terminal disclaimer.

(21) Appl. No.: 10/437,366

(22) Filed: May 12, 2003

(65) Prior Publication Data

US 2003/0212441 A1   Nov. 13, 2003

Related U.S. Application Data

(63) Continuation of application No. 09/768,207, filed on Jan. 22, 2001, now Pat. No. 6,564,105.

(60) Provisional application No. 60/177,414, filed on Jan. 21, 2000.

(51) Int. Cl.
  *A61N 1/08* (2006.01)

(52) U.S. Cl. .............................. 607/60; 607/30; 607/31

(58) Field of Classification Search ................ 607/60, 607/32, 31, 30, 3, 2, 72, 68; 128/903, 904; 600/300, 301, 302, 347, 365
See application file for complete search history.

(56) References Cited

U.S. PATENT DOCUMENTS 4,944,299 A   7/1990   Silvian (Continued)

FOREIGN PATENT DOCUMENTS

EP   0 346 783   6/1989

(Continued)

OTHER PUBLICATIONS

PCT International Search Report as issued in International Application No. PCT/US01/23003, Mailing Date Jul. 3, 2002.

(Continued)

*Primary Examiner*—Kennedy Schaetzle
(74) *Attorney, Agent, or Firm*—Foley & Lardner LLP

(57) ABSTRACT

An implanted medical device (e.g. infusion pump) and handheld communication device communicate with one another via telemetry wherein transmitted messages have enhanced numbers of and/or regularity of bit transitions to minimize the risk of synchronization loss between transmitted bits of data and received bits of data. Bit transitions for portions of messages may be enhanced by applying a pseudo-randomization scheme to those portions of messages that are transmitted in a way that allows the receiver to extract the original data from the received randomized data. Preferred randomization techniques modify (i.e. randomize) the data using a CRC value that is being accumulated while simultaneously causing the modified data to modify subsequent accumulation of the CRC itself. Upon reception, the reversal of data randomization occurs so that the intended message is appropriately received.

43 Claims, 7 Drawing Sheets

U.S. PATENT DOCUMENTS

| | | |
|---|---|---|
| 5,127,404 A | 7/1992 | Wyborny et al. |
| 5,191,326 A | 3/1993 | Montgomery |
| 5,368,562 A | 11/1994 | Blomquist et al. |
| 5,416,695 A | 5/1995 | Stutman et al. |
| 5,438,621 A | 8/1995 | Hornak et al. |
| 5,456,692 A | 10/1995 | Smith et al. |
| 5,630,710 A | 5/1997 | Tune et al. |
| 5,647,854 A | 7/1997 | Olsen et al. |
| 5,658,133 A | 8/1997 | Anderson et al. |
| 5,658,250 A | 8/1997 | Blomquist et al. |
| 5,659,299 A | 8/1997 | Williamson et al. |
| 5,669,877 A | 9/1997 | Blomquist |
| 5,695,473 A | 12/1997 | Olsen |
| 5,718,234 A | 2/1998 | Warden et al. |
| 5,788,669 A | 8/1998 | Peterson |
| 5,810,771 A | 9/1998 | Blomquist |
| 5,843,139 A | 12/1998 | Goedeke et al. |
| 5,876,370 A | 3/1999 | Blomquist |
| 5,935,099 A | 8/1999 | Peterson et al. |
| 5,935,106 A | 8/1999 | Olsen |
| 6,024,539 A | 2/2000 | Blomquist |
| 6,026,124 A | 2/2000 | Lee et al. |
| 6,123,686 A | 9/2000 | Olsen et al. |
| 6,219,580 B1 | 4/2001 | Faltys et al. |
| 6,564,105 B2 * | 5/2003 | Starkweather et al. ........ 607/60 |

FOREIGN PATENT DOCUMENTS

| | | |
|---|---|---|
| WO | WO 95/02426 | 1/1995 |
| WO | WO 96/03168 | 2/1996 |
| WO | WO 97/18639 | 5/1997 |

OTHER PUBLICATIONS

PCT International Search Report as issued in International Application No. PCT/US01/22926, Mailing Date Jul. 8, 2002.

* cited by examiner

```
/*****************************************************************/
/* This program generates the CCITT-16 bit CRC table for each    */
/* integer value from 0 to 255.                                  */
/* The polynomial is x^17+x^12+x^5+1, with a 0 initial seed.     */
/*****************************************************************/
#include <stdio.h>
#define POLY_CCITT16 0x1021
int crcfn(short int data, short int accum) {
  static int i;
  data <<= 8;
  for (i=8; i>0; i--) {
    if ((data ^ accum) & 0x8000)
      accum = (accum << 1) ^ POLY_CCITT16;
    else
      accum <<= 1;
    data <<= 1;
  }
  return accum;
}
void main() {
  short unsigned int crctable[256];
  short int i;
  printf("CRCTable16 ");
  for (i=0; i<256; i++) {
    crctable[i] = crcfn(i, 0);
    if (crctable[i] < 0x1000)
      printf("DW 0%xh\n", (int) crctable[i]);
    else if (crctable[i] > 0x9fff)
      printf("DW 0%xh\n", (int) crctable[i]);
    else
      printf("DW %xh\n", (int) crctable[i]);
  }
}
```

Figure 4

```
/* This program generates an 8 bit CRC table for each */
/* integer value from 0 to 255.                        */
#include <stdio.h>
#define POLY_8 0x31
int crcfn(unsigned char data, unsigned char accum) {
  static int i;
  for (i=8; i>0; i--) {
    if ((data ^ accum) & 0x80)
      accum = (accum << 1) ^ POLY_8;
    else
      accum <<= 1;
    data <<= 1;
  }
  return accum;
}
void main() {
  unsigned char crctable[256];
  int i;
printf("CRCTable8 ");
  for (i=0; i<256; i++) {
    crctable[i] = crcfn((unsigned char) i, (unsigned char) 0);
    if (crctable[i] < 0x10)
      printf("DB 0%xh\n", (int) crctable[i]);
    else if (crctable[i] > 0x9f)
      printf("DB 0%xh\n", (int) crctable[i]);
    else
      printf("DB %xh\n", (int) crctable[i]);
  }
}
```

Figure 5

METHOD AND APPARATUS FOR COMMUNICATING BETWEEN AN AMBULATORY MEDICAL DEVICE AND A CONTROL DEVICE VIA TELEMETRY USING RANDOMIZED DATA

RELATED APPLICATIONS

This is a Continuation Application and claims the benefit of prior filed U.S. Non-Provisional patent application Ser. No. 09/768,207 filed Jan. 22, 2001 now U.S. Pat. No. 6,564,105 by Timothy J. Starkweather et al. This application also claims the benefit of prior filed U.S. Provisional Patent Application No. 60/177,414; filed Jan. 21, 2000, by Ronald J. Lebel, et al., and entitled "Medical Apparatus and Method Including an Implantable Device and an External Communication Device". The entirety of this provisional application is hereby incorporated herein by this reference, including appendixes filed therewith and any references incorporated therein by reference, as if set forth in full herein.

FIELD OF THE DISCLOSURE

This invention relates generally to ambulatory medical devices and communication devices associated therewith that communicate with one another via a telemetry system and more particularly where at least portions of the data to be communicated are modified such that an increase in the number of bit transitions occur and/or the uniformity of bit transitions is improved (e.g. by randomizing the data).

BACKGROUND

Various ambulatory medical devices have been proposed and a number of such devices are commercially available. These devices include implantable infusion pumps, externally carried infusion pumps, implantable pacemakers, implantable defibrillators, implantable neural stimulators, implantable physiological sensors, externally carried physiologic sensors, and the like.

Implantable infusion pumps are generally configured to accept infusion commands from an external communication device via an RF telemetry system, or the like. These commands are, inter alia, used to set program variables that are in turn used in defining the quantity and/or timing that is used in supplying a drug to the patient. As the dispensing of appropriate amounts of the drug may be critical to the patient's well being, it is important that a reliable communication channel exist between the external communication device and the implantable device.

Implantable devices typically operate by battery power. The batteries may or may not be rechargeable. Higher consumption of power from an implantable device containing non-rechargeable batteries leads to a shortening of the usable life of implantable device and an associated increased frequency of surgery, potential pain, recovery, and inconvenience. Higher consumption of power from an implantable device containing rechargeable batteries leads to more frequent charging periods for the batteries and associated inconvenience and may lead to an overall shortening of the usable life of the implantable device. As such, whether or not an implantable device contains rechargeable batteries or non-rechargeable batteries, it is desirable to lower the power consumption of device. As telemetry reception and transmission are highly energy consumptive, it is desirable to minimize the operation time of telemetry reception and transmission modules. As such it is desirable to ensure that message length is kept to a minimum and that repeated transmissions and attempted receptions of previously sent but unsuccessfully received messages be kept to a minimum.

As such, a need exists in the field for improved reliability of message reception. More particularly, a need exists in the art for improved information transfer efficiency by the communication system while holding the time period that the communication system is powered to a minimum. Furthermore a need exists in the art to minimize the number of communication attempts that must occur to successfully complete transfer of a message.

Some digital communication receiving systems and methods depend on the regular receipt of bit transitions in order to maintain bit synchronization between the transmitter and the receiver. This dependency is not generally a problem when messages are short but can become problematic when message length increases as the message may contain extended portions where few or no bit transitions occur. The maximum message segment length for which synchronization can be retained without bit transitions occurring depends on the type of communication system being used and the difference in clocking frequency between the transmitter and receiver.

As such, a need exists in the field for an improved way of ensuring maintenance of bit synchronization between receiver and transmitter particularly while not increasing, or at least not significantly increasing, the length of a message that is necessary to convey a given quantity of information.

SUMMARY

A first object of certain aspects of the invention is to provide an ambulatory medical device and communication device with improved information transfer reliability.

A second object of certain aspects of the invention is to provide an ambulatory medical device and communication device with improved ability to maintain bit synchronization during reception of messages via telemetry.

A third object of certain aspects of the invention is to provide an ambulatory medical device and communication device with a telemetry system that transmits messages with an increased average number of bit transitions per bit transferred than found in the raw data to be transferred.

A fourth object of certain aspects of the invention is to provide an implantable medical device and communication device with a telemetry system that transmits messages with a more uniform average spacing of bit transitions than found in the raw data to be transferred.

A fifth object of certain aspects of the invention is to provide an ambulatory medical device and communication device with a telemetry system that transmits messages with at least a portion of the data randomized.

Other objects and advantages of certain aspects of the invention will be apparent to those of skill in the art upon review of the teachings herein. The various aspects of the invention set forth below as well as other aspects of the invention not specifically set forth below but ascertained from the teachings found herein, may address the above noted objects, or other objects ascertained from the teachings herein, individually or in various combinations. As such, it is intended that each aspect of the invention address at least one of the above noted objects or address some other object that will be apparent to one of skill in the art from a review of the teachings herein.

A first aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least some data portions of at least some messages are modified in preparation for transmission by the medical device or the communication device such that a higher number of bit transitions occur in the modified data than were found in corresponding data portions prior to preparation for transmission.

A second aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least some data portions of at least some messages are modified in preparation for transmission by the medical device or the communication device such that a more uniform spacing of bit transitions exist in the modified data than found in the corresponding data portions prior to preparation for transmission.

A third aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least some data portions of at least some messages are modified in preparation for transmission by the medical device or the communication device such that a more uniform distribution of byte patterns occur in the transmitted message than in the data portions prior to preparation for telemetry transmission.

A fourth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least some data portions of at least some messages are modified by a randomization algorithm in preparation for transmission from a first of the medical device or communication device to a second of the communication device or medical device.

A fifth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least a portion of the messages sent between the communication device and the medical device comprise a transmission preamble, an op-code for identifying the type of message being transmitted, a data portion, and an error checking code, wherein, on a predetermined basis, at least one segment of information is added to the data portion of the message prior to transmission by the medical device or the communication device and wherein the at least one segment of information comprises at least one bit.

In a specific variation of the fifth aspect of the invention, at least two bits with opposite values are added to the data portion within a prescribed number of bits of data to be transmitted.

In a specific variation of the fifth aspect of invention, the at least one segment is a plurality of segments and the plurality of segments of information are inserted at a known starting location and with fixed interval of bits between each insertion. In a further variation the inserted segments of information are one bit each. In an alternative further variation, the segments of information inserted are at least two bits each. In a further variation the at least two bits include bits of opposite value.

In an additional specific variation of the fifth aspect of the invention, the at least one segment is a plurality of segments and each of the plurality of segments of information is inserted when a predefined number of consecutive bits of data to be transmitted lack a transition and wherein at least one inserted bit has a bit value that is opposite in value to the number of consecutive bits that lacked a transition. In a further variation the inserted segments of information are one bit each. In an alternative further variation, the segments of information inserted are at least two bits each. In a further variation the at least two bits include bits of opposite value.

A sixth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least some data portions of at least some messages have a maximum separation between bit transitions reduced.

Additional specific variations, provide the medical devices of each of the above aspects and above noted variations as implantable devices such as implantable infusion pumps, implantable physiological sensors, implantable stimulators, and the like, or external devices such as subcutaneous delivery infusion pumps or sensors that ascertain a physiological parameter or parameters from subcutaneous tissue or from the skin of the patient. Such infusion pumps may dispense insulin, analgesics, neurological drugs, drugs for treating AIDS, drugs for treating chronic ailments or acute ailments. Sensors may be used to detect various physiological parameters such as hormone levels, insulin, pH, oxygen, other blood chemical constituent levels, and the like. The sensor may be of the electrochemical type, optical type, and may or may not be enzymatic in operation.

In even further variations of the above noted aspects, and above noted variations, one or more of the following is provided: (1) a first portion of the MD telemetry system is incorporated into the MD processor and a second portion of the MD telemetry system is external to the MD processor, (2) a first portion of the CD telemetry system is incorporated into the CD processor and a second portion of the CD telemetry system is external to the CD processor, (3) the MD processor includes an MD central processing unit and at least one other MD functional module, (4) the CD processor includes a CD central processing unit and at least one other CD functional module, (5) the MD electronic control circuitry includes at least one external MD functional module, other than a portion of the MD telemetry system, that is external to the MD processor, or (6) the CD electronic control circuitry includes at least one external CD functional module, other than a portion of the CD telemetry system, that is external to the CD processor.

Additional aspects of the invention set forth method counterparts to the above system aspects as well as to other functional associations and relationships, and processes that have not been specifically set forth above but will be understood by those of skill in the art from the disclosure set forth herein.

Further aspects of the invention will be understood by those of skill in the art upon reviewing the teachings herein. These other aspects of the invention may involve various combinations of the aspects presented above as well as to other configurations, that have not been specifically set forth above.

BRIEF DESCRIPTION OF THE DRAWINGS

The above referred to objects and aspects of the present invention will be further understood from a review of the following description, drawings, and claims set forth hereafter, wherein:

FIG. 4 depicts a computer program written in the C-language for generating a 16 bit CRC table;

FIG. 5 depicts a computer program written in the C-language for generating an 8 bit CRC table;

DETAILED DESCRIPTION OF PREFERRED EMBODIMENTS

Figure 1A:
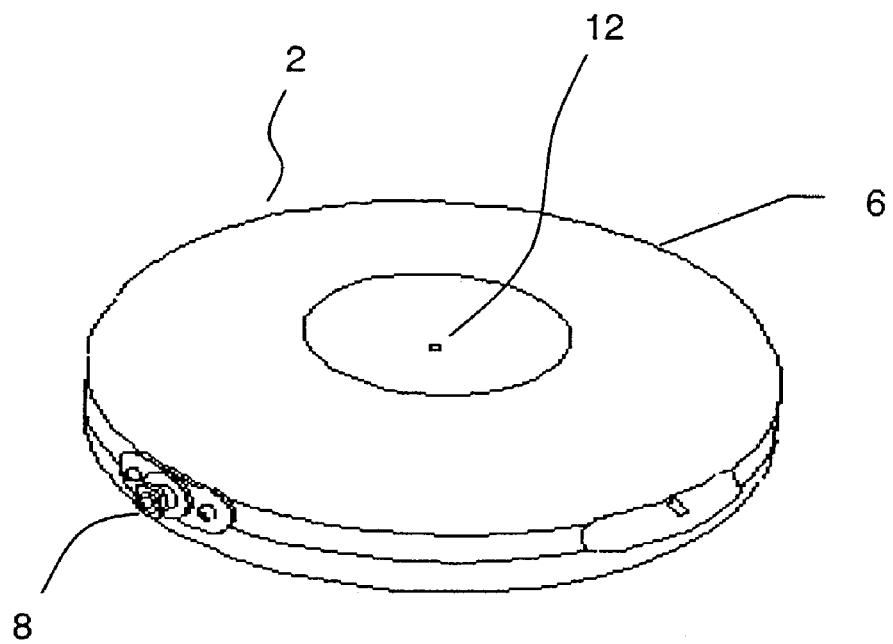
FIG. 1a depicts a perspective view of the main body of the implantable device of the first preferred embodiment.

Various details about the structural and functional configuration and operation of preferred ambulatory medical devices and preferred communication devices are found in several U.S. patent applications filed concurrently herewith and incorporated herein by reference in their entireties: (1) Ser. No. 09/768,045, (2) Ser. No. 09/768,202, (3) Ser. No. 09/768,206, (4) Ser. No. 09/768,198, and (5) Ser. No. 09/768,221.

U.S. patent application Ser. No. 09/768,045, filed on Jan. 22, 2001 (concurrently herewith), by Starkweather, et al., entitled "Ambulatory Medical Apparatus and Method Having Telemetry Modifiable Control Software", corresponding to Medical Research Group, Inc., is hereby incorporated herein by this reference as if set forth in full herein. This application provides teachings concerning an implantable medical device (e.g. infusion pump) and handheld communication device wherein the implantable device is capable of operating under control of different software programs, wherein a first program operates after resetting the implantable device and is not capable of allowing significant medical functionality but is capable of selected telemetry operations including telemetry operations that allow replacement software to be downloaded, and wherein a second program may be caused to take control of the device and enables medical functionality and selected telemetry operations but is incapable of receiving replacement software. It is also taught that a software image may be received in multiple messages where each message is provided with its own validation code and wherein a validation code for the whole image is provided and wherein each provided validation code must be compared to a derived validation code prior to accepting the validity of the replacement software.

U.S. patent application Ser. No. 09/768,202, filed on Jan. 22, 2001 (concurrently herewith), by Lebel, et al., entitled "Ambulatory Medical Apparatus and Method Using a Robust Communication Protocol", corresponding to Medical Research Group, Inc., is hereby incorporated herein by the references as set forth in full herein. An implanted medical device (e.g. infusion pump) and external device communicate with one another via telemetry wherein messages are transmitted under a robust communication protocol. The communication protocol gives enhanced assurance concerning the integrity of messages that impact medical operations of the implantable device. Messages are transmitted using a multipart format that includes a preamble, a frame sync, a telemetry ID, data, and a validation code. The data portion of the message includes an op-code that dictates various other elements that form part of the message. The data portion may also include additional elements such as sequence numbers, bolus numbers, and duplicate data elements. A telemetry ID for the transmitting device may be implicitly embedded in the message as part of the validation code that is sent with the message and that must be pre-known by the receiver to confirm the integrity of the received message.

U.S. patent application Ser. No. 09/768,206, filed on Jan. 22, 2001 (concurrently herewith), by Bowman, et al., entitled "Ambulatory Medical Apparatus and Method using a Telemetry System with Predefined Reception Listening Periods", corresponding to Medical Research Group, Inc., is hereby incorporated herein by the reference as if set forth in full herein. This application provides teachings concerning an implantable medical device (e.g. infusion pump) and an external device that communicate with one another via telemetry messages that are receivable only during listening windows. Each listening window is open for a prescribed listening period and is spaced from other listening windows by an interval. The listening period is typically kept small to minimize power consumption. To increase likelihood of successful communication, the window may be forced to an open state, by use of an attention signal, in anticipation of an incoming message. To further minimize power consumption, it is desirable to minimize use of extended attention signals, and this is accomplished by the transmitter maintaining an estimate of prescribed listening start times and attempting to send messages only during listening periods. In the communication device, the estimate is updated as a result of information obtained with the reception of each message from the medical device.

U.S. patent application Ser. No. 09/768,198, filed on Jan. 22, 2001 (concurrently herewith), by Lebel, et al, entitled "Ambulatory Medical Apparatus with Hand Held Communication Device", corresponding to Medical Research Group, Inc., is hereby incorporated herein by this reference as if set forth in full herein. This application provides teachings concerning an implantable medical device (e.g. infusion pump) and handheld communication device (CD) that exchange messages via telemetry such that commands are supplied to the implantable device and operational information is obtained therefrom. The CD is controlled, at least in part, by a processor IC according to a software program operating therein and provides feedback to a user via a visual display, an audio alarm, and a vibrational alarm, and allows input from the user via a touch sensitive keypad. Certain input functions are restricted by password. The visual display includes an icon and fixed element display region and a bitmap display region. The fixed element display region includes time and date displays, battery and drug level displays that decrement, and a moving delivery state display. Various screens allow operational or log information to be displayed and/or user entry of commands. Program features when disabled are removed from a series of screen options that can be scrolled through.

U.S. patent application Ser. No. 09/768,221. filed on Jan. 22, 2001 (concurrently herewith), by Lebel, et al., entitled "Microprocessor Controlled Ambulatory Medical Apparatus with Hand Held Communication Device", corresponding to Medical Research Group, Inc., is hereby incorporated herein by this reference as if set forth in full herein. This application provides teachings concerning an implantable medical device (e.g. infusion pump) and handheld communication device, wherein an implantable infusion pump possesses operational functionality that is, at least in part, controlled by software operating in two processor ICs which are configured to perform some different and some duplicate functions. The pump exchanges messages with the external communication device via telemetry. Each processor controls a different part of the drug infusion mechanism such that both processors must agree on the appropriateness of drug delivery for infusion to occur. Delivery accumulators are incremented and decremented with delivery requests and with deliveries made. When accumulated amounts reach or exceed, quantized deliverable amounts, infusion is made to occur. The accumulators are capable of being incremented by two or more independent types of delivery requests. Operational modes of the infusion device are changed automatically in view of various system errors that are trapped, various system alarm conditions that are detected, and when excess periods of time lapse between pump and external device interactions.

The first embodiment of the present invention provides a long term implantable medical delivery system that controllably supplies insulin to the body of a patient afflicted with diabetes mellitus. This embodiment includes an implantable medical device and an external communication device. In the most preferred embodiments, the communication device is a hand held device that is used directly by the patient to interact with the medical device as opposed to being limited to use by a physician, nurse, or technician. It is preferred that the communication device provide (1) the ability to send commands to the medical device, (2) receive information from the medical device, and (3) be able to present to the patient at least a portion of the information it receives from the medical device. In preferred embodiments, the patient interacts with the medical device via the communication device at least once per week, on average, more preferably at least once every other day, on average, and most preferably at least once per day, on average.

The implantable medical device (MD) includes a biocompatible housing; a reservoir within the housing for holding a quantity of insulin; a side port that attaches to the side of the housing, a catheter, that connects to the side port; a pumping mechanism, within the housing, for moving the insulin from the reservoir through the catheter to the body of the patient; and control, monitoring, and communication electronics located within the housing. In alternative embodiments various portions of the implantable device hardware may be located outside the housing. For example, the pumping mechanism or a telemetry antenna may be located within the side port; or a telemetry antenna may be mounted on the outside surface of the housing, or extend along, the catheter.

The external communication device (CD) communicates commands to the medical device, receives information from the medical device, and communicates system status and system history to the patient. The external communication device includes a housing; a keypad mounted on the housing; a display forming part of the housing; and control, monitoring, and communication electronics located within the housing. In alternative embodiments, the keypad may be replaced in whole or in part by a touch sensitive display or a voice recognition system. In addition, or alternatively, the display may be replaced in whole or in part by a speech generation system or other audio communication system.

Figure 1B:
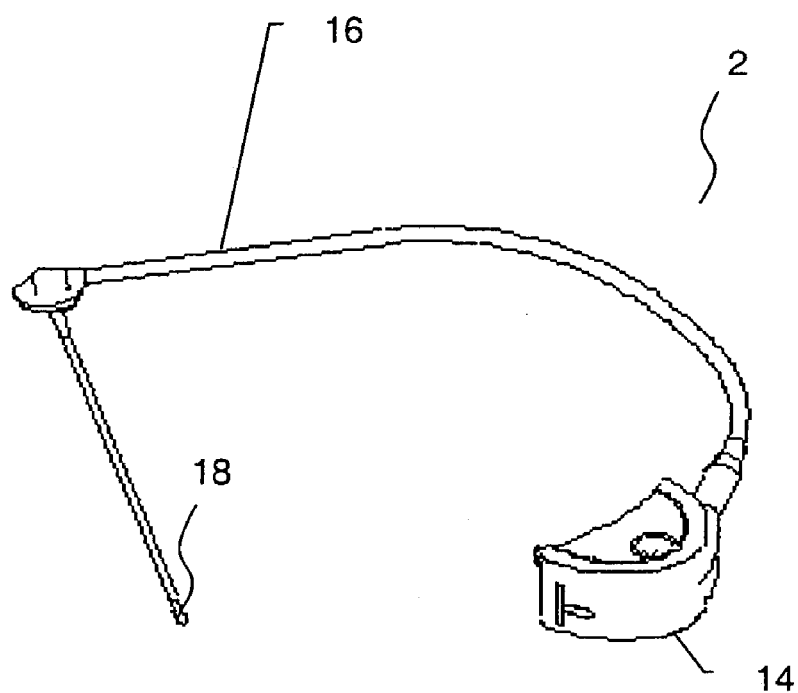
FIG. 1b depicts a perspective view of the catheter assembly that attaches to the main body of the implantable device of the first preferred embodiment.

The outer appearance of the implantable device 2 is depicted in two pieces in FIGS. 1*a* and 1*b* and includes housing 6 having a drug outlet port 8, and a refill port 12, a removable sideport 14 that mounts against the side of the housing 6 over outlet port 8, and a catheter 16 having a distal end 18 and a proximal end that attaches to sideport 14. In alternative embodiments, the implantable device may take on a different shape and/or the sideport may be removed in favor of a permanently mounted catheter assembly.

Figure 2:
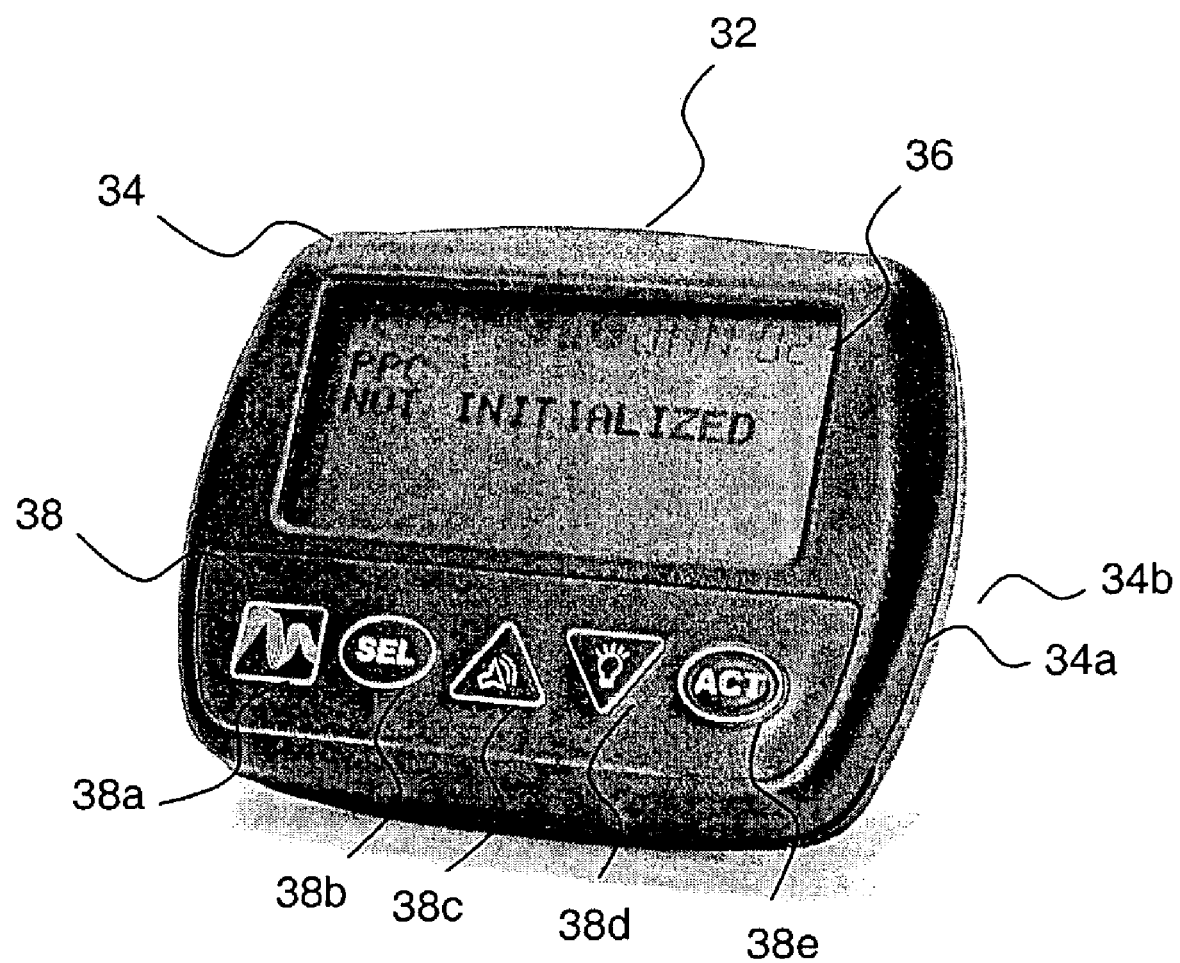
FIG. 2 depicts a perspective view of external communication device of the first preferred embodiment.

The outer appearance of the external communication device 32 is depicted in FIG. 2. The various components of the external communication device are fitted in or on housing 34. Housing 34 is divided into a front portion 34a and a back portion 34b. The front portion is provided with an opening in which an LCD panel 36 is positioned. The panel 36 has a lower portion that is a bit map display and an upper portion that provides icons and fixed element displays. The front portion of the external communication device is also provided with a five-element keypad 38. A first key 38a is not located under a raised pad and does not provide tactile feedback when it is touched and is used only for special functions. The remaining four keys 38b, 38c, 38d, and 38e have raised pads that provide tactile feedback when they are depressed. These remaining keys are used in normal operation and are known as the select key, the up arrow key, down arrow key, and the activate key, respectively. The back of the housing is fitted with a door under which a compartment is located for holding a replaceable battery.

Figure 3:
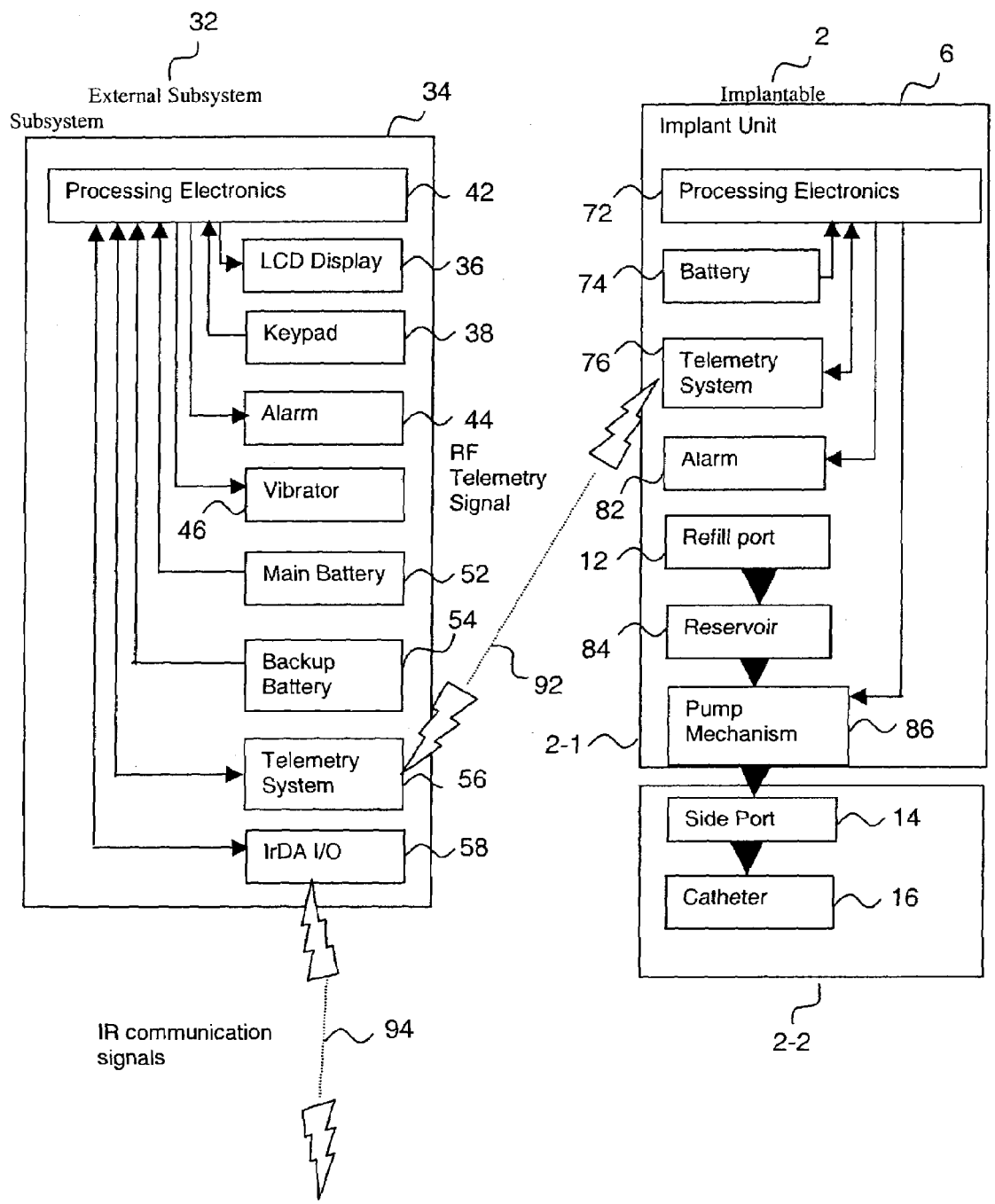
FIG. 3 depicts a block diagram of the main components/modules of both the implantable device and the external communication device of the first preferred embodiment.

FIG. 3 depicts a simplified block diagram of various functional components or modules (i.e. single components or groups of components) included in the implantable medical device 2 and external communication device 32. The external communication device 32 includes (1) a housing or cover 34 preferably formed from a durable plastic material, (2) processing electronics 42 including a CPU and memory elements for storing control programs and operation data, (3) an LCD display 36 for providing operation for information to the user, (4) a keypad 38 for taking input from the user, (5) an audio alarm 44 for providing information to the user, (6) a vibrator 46 for providing information to the user, (7) a main battery 52 for supplying power to the device, (8) a backup battery 54 to provide memory maintenance for the device, (9) a radio frequency (RF) telemetry system 56 for sending signals to the implantable medical device and for receiving signals from the implantable medical device, and (10) an infrared (IR) input/output system 58 for communicating with a second external device.

The second external device may include input, display and programming capabilities. The second device may include a personal computer operating specialized software. The computer may be used to manipulate the data retrieved from the communication device or the medical device or it may be used to program new parameters into the communication device or directly into the medical device, or even used to download new software to the communication device or to the medical device. The manipulation of the data may be used in generating graphical displays of the data to help aid in the interpretation of the data. Such data interpretation might be particularly useful if the medical device provides data concerning a physiological parameter of the body of the patient, such as a glucose level versus time. More particularly the computing power and display attributes of the second device might be even more useful when the medical device includes both an implanted sensor (e.g. glucose sensor), or external sensor, and an implanted pump (e.g. insulin pump), or external pump, where the second external device may be used to enhance the ability to ascertain the effectiveness of the two devices working together. Successful control periods and problem control periods could be more readily identified. In fact, if the two devices work on a closed loop basis or semi-closed loop basis, the analysis performable by the second external device may be useful in deriving new closed loop control parameters and/or in programming those parameters directly into the communication device or the medical device or devices.

The implantable device 2 includes (1) a housing or cover 6 preferably made of titanium that may or may not be coated to enhance biocompatibility, (2) processing electronics 72 including two CPUs and memory elements for storing control programs and operation data, (3) battery 74 for providing power to the system, (4) RF telemetry system 76 for sending communication signals (i.e. messages) to the external device and for receiving communication signals (i.e. messages) from the external device, (5) alarm or buzzer 82 for providing feedback to the user, (6) refill port 12 for accepting a new supply of drug as needed, (7) reservoir 84 for storing a drug for future infusion, (8) pumping mechanism 86 for forcing selected quantities of drug from the reservoir through the catheter to the body of the patient, (9) sideport 14 for providing a replaceable connection between the (10) catheter and the pump housing and for allowing diagnostic testing of the fluid handling system to occur, and catheter 16 for carrying medication from the implant location to the desired infusion location.

In this embodiment, the pump mechanism is preferably a low power, electromagnetically driven piston pump. Such as for example Model Nos. P650005 or P650009 as sold by Wilson Greatbatch Ltd. of Clarence, N.Y. which have stroke volumes of 0.5 microliters and draw under 7 mJ (e.g. about 6 mJ) per pump stroke and under 4 mJ (e.g. about 3 mJ) per pump stroke, respectively. The pump mechanism dispenses a sufficiently small volume of insulin per stroke so that a desired level of infusion resolution is achieved. For example if an infusion resolution of 0.2 units of insulin were desired when using U400 insulin, then a stroke volume of about 0.5 microliters would be appropriate. In other embodiments other types of infusion pumps may be used, e.g. peristaltic pumps, screw driven pumps, and the like.

As depicted in FIG. 3, the implantable device includes a reservoir 84 for holding a desired quantity of insulin. In this embodiment, the drug held in the reservoir is preferably maintained at a slight negative differential pressure (with respect to the pressure on the outside of the housing) so that in the event of a leakage in the reservoir 84 or housing 6, the drug will not be forced from the housing into the body of the patient. The drug is added to the reservoir 84 by means of a transcutaneous needle that is passed from a position exterior to the body into self sealing refill port 12. Due to the slight negative pressure that the reservoir experiences, insulin in a syringe connected to the needled is drawn into the reservoir without need of external force. The drug is extracted from the reservoir 84 and forced through catheter 16 by an electronically controlled pump mechanism 86. In alternative embodiment positive pressure reservoirs may be used in combination with pumping mechanisms that force the medication or drug from the implantable device and/or used with flow restrictors that dispensed the drug at a fixed rate or at a variable rate with the aid of valves or flow diverters.

The size of the reservoir is preferably large enough to hold sufficient insulin so that refilling does not have to occur too often. For example, it is preferred that time between refills be within the range of 1.5–4 months or longer, more preferably at least 2 months, and most preferably at least 3 months. Opposing the containment of a large volume of insulin, is the desire to keep the implantable device as small as possible. In the present embodiment the implantable device and reservoir has been designed to hold about 13 ml of insulin. A preferred insulin has a concentration of 400 units per milliliter and is available from Aventis HOE 21Ph U-400 from Aventis Pharma (formerly Hoechst Marion Roussel AG, of Frankfurt am Main, Germany). This insulin is a highly purified, semi-synthetic human insulin with 0.2% phenol as a preserving agent, glycerol as an isotonic component, TRIS as a buffer, plus zinc and Genopal® as stabilizing agents. This quantity and insulin concentration allows about 2–4 months between refills. In other embodiments higher insulin concentrations may be used (e.g. U-500 or U-1000) to increase time between refills or to allow reduction in reservoir size. In some embodiments, when higher concentrations are used, any quantized minimum delivery amounts may be reduced by modifying the pumping mechanism, control circuitry, or software control algorithm so that infusion resolution is not adversely impacted.

The external communication device contains appropriate software to provide proper control of the device including appropriate functionality to allow communication with the implantable medical device, to allow adequate control of the operation of the implantable device, and to give appropriate feedback to the user regarding overall system operation. The implantable device is provided with appropriate software to allow communication with the external communication device, to allow safe and appropriate operation of the medical functionality of the implantable device, and to allow direct feedback to the user concerning implantable device status via the internal alarm.

The control electronics of both the implantable device and external communication device are centered around microprocessor based integrated circuits, i.e. processor ICs, that are implemented in the present embodiment in the form of application specific integrated circuits (ASICs). Two such ASICs are used in the implantable device to increase operational safety of the device by configuring the device to require that the two ASICs act in conjunction with each other in order for medication infusion to occur.

In different embodiments, more or less of the control electronics may be implemented within one or more processor ICs while any remaining portions may be implemented external to the processor IC(s). The processor IC may be referred to as an MD processor if used in the medical device portion of the system or a CD processor if used in the communication device portion of the system. In other embodiments the process IC used in the communication device may be different, e.g. have a different CPU or different peripheral modules, from a processor IC used in the medical device. In embodiments where more than one processor IC is used in either the medical device or the communication device each of the processors may be different. They may be specifically designed for their intended roles when they perform at least partially different functions. Depending on particular design constraints portions of the electronics not embodied in the processor ICs may form part of one or more hybrid circuit boards or be otherwise mounted within, on, or even in some cases external to a device housing.

Each processor IC of the present embodiment includes a 16-bit core CPU which is a CMOS low power version of the INTEL 8086 processor and various peripheral modules that are used for system control, data acquisition, and interfacing with electrical components external to the processor IC.

The peripheral modules of the processor IC include (1) a non-volatile memory interface module, e.g. a SEEPROM interface module, (2) a boot ROM module; (3) an SRAM module; (4) a memory decoder module; (5) a crystal oscillator module; (6) a timer module; (7) a pump interface module; (8) a watchdog module; (9) an RF module; (10) an interrupt handler module; (12) an analog-to-digital converter module; (13) an LCD clock driver module; (14) an alarm interface module; and (15) first and second synchronous serial interface modules.

In alternative embodiments fewer, additional, or different peripheral modules may be incorporated into the processor ICs. In one extreme the processor IC may simply incorporate a CPU with all other modules being external thereto. In the other extreme almost all, if not all, electronic components may be incorporated into a single processor IC. Intermediate alternatives might incorporate a single additional module into the processor IC (in addition to the CPU), others might incorporate more than one, e.g. 4 or more, 8 or more, or the like. In still other alternatives, the number of peripheral modules or components in an entire device may be considered and more than a certain percentage of them incorporated into one or more processor ICs, e.g. more than 50%, more than 75%, or even more than 90%.

The processor ICs are responsible for basic system management and communication of information between the implantable device and the external communication device through the RF telemetry link. The telemetry systems of the present embodiment are implemented in part through electrical hardware and in part through software controlled by a processor IC.

In the present embodiment, most of the required electrical modules for the implantable device are integrated within the processor ICs. However, several are not. These additional modules include two independent crystal oscillators (one for each ASIC); two non-volatile memory modules (one for each ASIC), e.g. SEEPROM chips; a volatile memory module (used only by one of the ASICs), e.g. an SRAM chip; pump driver circuitry (partially controlled by the each ASIC); front end telemetry system circuitry; and voltage measurement circuitry associated with the pump driver circuit; a buzzer; and a battery.

Within the implantable device telemetry operations are controlled by a single ASIC (sometimes known as the main processor) The other processor (sometimes known as the monitor processor) controls the buzzer and is thus responsible for audio communications coming from the implantable device. The medical functionality of the implantable device (i.e. the administration of insulin in the present embodiment) is controlled by both processors. To maintain the implantable device in a fail safe operational mode, these two processors maintain an appropriate level of agreement concerning infusion instructions an error condition results and either pumping is halted or a system reset may be made to occur. The main and monitor processors communicate with each other through the use of hardwired serial input and output ports.

As with the implantable device, the control electronics of the external communication device are centered around an ASIC that controls and interacts with a number of peripheral modules. These peripheral modules include an LCD display and driver, an IR port and driver, a crystal oscillator, a keypad and keypad interface, power management modules and reset circuitry, external volatile memory (e.g. SRAM) and non-volatile memory (e.g. SEEPROM), a buzzer, and front end telemetry hardware.

The telemetry system for the implantable device and the external communication device provide a half-duplex link between each other using a carrier frequency of about 250 kHz (e.g. about $2^{18}$ Hz) and a data signal having a frequency of about 8 kHz (e.g. about $2^{13}$). The transmitter hardware uses the 8 kHz data signal to modulate the carrier signal to generate signals that will be transmitted by the antenna. The receiver hardware receives the modulated signal and demodulates it to extract the 8 kHz data signal. Both the implantable device and the external communication device have transmit and receive capabilities to allow two-way communication.

Most of the RF telemetry circuits necessary for communication between the external communication device and the implantable device are implemented in the processor IC. In order to minimize the digital noise interference that the processor IC might impart to the weak RF signals that are being received, a high-gain RF amplifier is implemented off-chip. Also an RF antenna, that is used for both transmission and reception, and circuitry to select between reception and transmission are implemented off-chip. The remaining analog sections and all the digital demodulation circuits are implemented in the processor IC.

The RF module of the processor IC outputs in phase and quadrature phase signal components for combined transmission by the external antenna. The RF module also supplies a control signal that is used to switch between a transmission configuration and a reception configuration. The RF module receives as inputs signals from the amplification circuitry.

A Quadrature Fast Acquisition Spread Spectrum Technique (QFAST®) is used as the modulation technique. QFAST® modulation is based on an Offset Quadrature Phase Shift Keying (QPSK) modulation technique. In this technique, data generated by the CPU modulates clock signals at the carrier frequency. As a result of quadrature modulation, in-phase and quadrature-phase components of the given data stream are generated. The two components are then applied to opposite ends of the external antenna so that a combined signal is transmitted.

As noted above, external to the processor IC, the received RF signal is amplified by a high gain receive amplifier. A bandpass filter is used to attenuate out-of-band components such as those due to AM radio stations. The amplified RF signal then enters a mixer in the RF module of the processor IC and is converted to baseband using two mixers, one in-phase mixer and one quadrature phase mixer both at the carrier frequency. The mixer outputs are the quadrature components of the baseband signals. An integrator & dump function in the RF module then removes the sum frequency (2fc) and high frequency noise (i.e. acting as a low pass filter) from each of the two signals. The processed signals are then digitized using a comparator and passed to the demodulator where the data and clock are recovered.

In QFAST®, data rate adaptability is accomplished through a spread-spectrum "coding gain" concept, with the spreading code being a simple clock. The modulation produced by the QFAST® modulator is demodulated in a manner which delivers both clock and data. All of the QFAST® modulation and demodulation circuits are digital and are incorporated into the processor IC.

The QFAST® technique provides a communication system with a number of attributes: (1) it extracts the clock from the received signal without a clock recovery loop; (2) it provides demodulation of data without phase ambiguity and without the requirement for synchronous demodulation; (3) it makes effective use of the available transmission bandwidth, (4) it results in fast acquisition of the message signal; (5) it is relatively immune to the effects of highly dispersive and distorting propagation media; (6) it does not require regeneration of a phase-coherent local replica at the receiver of the transmitted carrier; (7) it does not require resolution of ambiguity between the in-phase and quadrature-phase channels in the receiver; and (8) it does not exhibit data phase ambiguity.

Further detail about QFAST® (Quadrature Fast Acquisition Spread Spectrum Technique) may be found in U.S. Pat. No. 5,559,828, entitled Transmitted Reference Spread Spectrum Communication Using a Single Carrier with Two Mutually Orthogonal Modulated Basis Vectors, by Armstrong, et al.

The RF module in the processor IC consists of timing circuitry, circuitry to maintain time synchronization between the implantable device and the external communication device, a digital RF transmitter section that includes a QFAST® RF modulation transmitter, an analog receive module, and a digital receive section that includes a QFAST® RF modulation receiver.

As noted above, the implantable device and the external communication device communicate with each other through an RF telemetry system. The communication occurs in the form of messages (i.e. communication signals or packets) that are passed between the two devices. These messages have a multi-part format: (1) preamble, (2) frame sync, (3) telemetry identifier, and (4) data. In alternative embodiments, other formats may be used including formats that simply change the order of the above noted elements, formats that dispense with one or more of the above elements, formats that add in additional elements or elements that replace one or more of the above noted elements.

For communications from the implantable device to the external communication device the preamble is a repeating pattern of for example "10", i.e. 10101010. This alternating pattern of ones and zeros is broadcast for 8 bit times. This pattern is considered the standard preamble pattern. In other embodiments the standard preamble pattern may be different (e.g. it may be a repeated pattern of "01" instead of "10"). The standard preamble need not utilize a pattern that results in a bit transition with the transmission of each bit though frequent bit transitions are preferred, as a certain number of bit transitions are considered necessary to establish bit synchronization, and thus the more transitions the shorter the minimum length that the preamble must possess.

For communications from the external communication device to the implantable device, the preamble is either of the standard preamble pattern, but applied for an extended number of bit times (e.g. 24), or is of an attention preamble pattern that is applied for, typically, even a longer extended number of bit times. In other embodiments, not only may the preamble used by the implantable device and the external communication device have different lengths as illustrated in this embodiment, they may also use different standard preamble bit patterns. Of course in still other embodiments, the same preamble length may be used by both the implantable device and the external communication device whether or not the same standard preamble bit pattern is used. In this first preferred embodiment, the attention preamble pattern is formed of a repeated pattern of "110", i.e. 110 . . . 110. In other embodiments, other attention preamble patterns may be used (e.g. repetitions of "011", "100", "001", "1011", and the like.

The preamble, whether of the standard pattern or the attention pattern, is used so that the RF reception hardware can establish bit synchronization (i.e. bit boundary recognition) of the incoming data. However, the attention preamble is further used to get and hold the receiver's attention. As long as the attention preamble is being received, the receiver's telemetry hardware stays on and continues to track the signal. In other embodiments, the concept of a standard preamble pattern that will not hold the receiver's attention may be dispensed with in favor of always using a preamble that is in effect an attention preamble.

The attention preamble is considered to be lost, or no longer being received, when the receiver receives more than 2 inappropriate bit values during receipt of any 64 bits or when a frame sync pattern is received. The receiver loads the bits received into a shift register and compares the shifting pattern of bits with a frame synchronization pattern (i.e. frame sync pattern). After attention is believed to be lost the receiver stays on and continues to look at a number of bits (e.g. up to the number making up frame sync) to confirm whether the frame synchronization pattern is received.

Of course in other embodiments, the error tolerance believed acceptable may be increased or decreased or defined in a different manner. For example instead of using an error tolerance of 2 bits out of 64 bits, one might use a tolerance of $1/32$. The tolerance may even be increased to $2/32$, $3/64$, $4/64$, or even higher. Alternatively, it may be decreased to $1/64$, $1/128$ or even to zero.

As such, the attention preamble may be used when there is some uncertainty in the time synchronization of the implantable and external communication devices.

The extra bit length of the attention preamble allows the receiver's reception window to open a little late, relative to the transmitter's initiation of transmission, and to still have the receiver pick up the entire message. Furthermore, the extra bit length of the attention preamble allows the receiver's reception window to open a little earlier relative to the transmitter's initiation of transmission and still have the receiver's attention locked onto the preamble and have the reception window remain open as long as the attention preamble is being received in anticipation of receiving a frame sync pattern.

The receiver may miss some of the initial bits in the Preamble but a minimum number of bit transitions (e.g. 4, 6, or 8 transitions) of the Preamble Pattern must be received to ensure bit synchronization between the transmitted message and the receiver. In the present embodiment, as power reserves in the implantable device are considered more critical than power reserves in the external communication device, it is considered more acceptable to open the external communication device's listening window a little earlier and leave it open a little longer than a best estimate as to when transmission from the implantable device may occur so that whenever a communication comes from the implantable device the external communication device may be in condition to receive it without excessive burden on the implantable device power reserves. In this regard, the implantable device broadcasts with a minimal preamble size in order to reduce power consumption within the implantable device. In other embodiments, the preamble used by the implantable device may be larger relative to the minimum number of bit transitions needed to establish bit synchronization.

In the present embodiment, frame sync may actually be considered byte sync (i.e. frames are bytes) and is a single byte of a selected pattern and is used so the receiver can obtain byte boundaries for the transmitted data. In the present embodiment, the selected pattern is 10110000. In other embodiments, other patterns, pattern lengths, and frame sizes may also be acceptable so long as the patterns (in combination with preamble or attention preamble patterns and any tolerances in their reception) will not lead to errors in defining byte transitions. In still other embodiments, the attention preamble pattern may be of the same bit pattern as the frame sync, in which case, some error tolerance may be allowed in the frame sync pattern and the receiver's attention would be held until the pattern is lost or a valid telemetry identification pattern is received.

In the present embodiment, the telemetry identifier (i.e. telemetry ID) is a 3-byte value that is used to ensure that only the intended receiver receives a message. The value of all "1s" indicates a universal message that is to be received by all receivers, otherwise the Telemetry ID must be agreed upon between the receiver and transmitter. In this first embodiment, a unique telemetry ID is provided for each implantable device and each external communication device during manufacturing. In the present embodiment only the external communication device can transmit a message using the universal telemetry ID code. In the present embodiment, the telemetry IDs that the receiver will consider to be valid are its own telemetry ID or the universal telemetry ID. All other incoming bit patterns will be rejected with the result that the receiver will be either turned off or will start again looking for a valid frame sync pattern. In alternative embodiments, instead of the receiver accepting only its own telemetry ID (in addition to the universal telemetry ID) it may instead accept the telemetry ID of the transmitter if it has been married (i.e. linked) to that transmitter. In other alternative embodiments, a different length telemetry identifier may be used by the implantable device and the external communication device. In still further alternatives, the telemetry IDs may not be unique particularly when it is believed that the chance of miscommunication between devices is not a significant risk. In fact, if there is little risk of miscommunication, telemetry ID may be dropped from the message protocol.

In the present embodiment, after receipt of the frame sync, the incoming bit values in a message being received are compared to the two valid telemetry ID patterns to determine if the message is intended for the receiver. If a valid telemetry ID is received, the receiver listens for the remaining portion of the message. In alternative embodiments the frame sync and telemetry ID may be combined into a single entity that is identified as a whole as opposed to the present embodiment where the two pieces are looked for and identified separately.

In the present embodiment, data is provided as an integer number of bytes following the telemetry ID. In the present embodiment the first byte of the data indicates the message type. This first byte of data is an operation code or op-code. Each op-code, based on its nature, is followed by data having a known length in bytes. As such, based on the op-code, the receiver knows exactly how many more bytes of data to listen for. After receiving those bytes, the receiver may be turned off to conserve power. In the present embodiment, the data portion of the message ends with a one or two byte error checking code (whether it is one byte or two bytes is defined by the particular op-code received). The error checking code of this embodiment is in the form of a cyclic redundancy code (CRC). In other embodiments, the CRC may be replaced with another error checking code and/or it may be placed in a different part of the message or even deleted from the message protocol completely. The op-code may also be placed in another part of the message, it may be followed by an additional segment of the message that explicitly indicates the message length, or it may be deleted in favor of other techniques that may be used in interpreting the message and for determining when the end of the message has been properly received.

In the present embodiment, the telemetry system may lose bit synchronization if insufficient bit transitions are received per unit time (e.g. if more than about 100 to 120 bit times lapse without receiving a transition). In order to ensure that a sufficient number of bit transitions occur, the data portion of the message, with the exception of the op-code is randomized prior to transmission and is de-randomized upon receipt. In alternative embodiments, at the cost of sending more data, instead of randomizing the data, periodic bytes of data with known transitions may be added to the protocol (e.g. after every fifth or tenth byte of data a byte, or at least several bits, may be transmitted for the purpose of ensuring that bit synchronization is maintained). In further alternatives, as short messages may not be subjected to improper reception due to loss if bit synchronization, randomization may be limited to use with longer messages (e.g. messages with data portions longer than 10–15 bytes).

In the present embodiment, depending on the type of message, a 1 or 2-byte cyclical redundancy code (CRC) follows the data bytes. It is preferred that the CRC be generally computed using the telemetry ID of the message originator (i.e. the telemetry ID of the transmitter). This serves as a form of security. If a message with this type of CRC is received by an implantable device, the implantable device must know the telemetry ID of the transmitting external communication device or the implantable device will reject the message because of a CRC error.

A CRC to be included with a message, in the present embodiment, is calculated based on the successive bytes forming the message and possibly upon the identity of the transmitter as well. When the CRC is computed using the telemetry ID of the message originator, the first three bytes used in the calculation are the telemetry ID of the originator. The CRC calculation then uses the three bytes of the telemetry ID of the intended receiver, the one byte of op-code, and then the remaining bytes of data in the message (with the exception of the CRC itself that is being calculated). When the CRC is not computed with the message originator's telemetry ID, the CRC is computed based on the bytes of the message starting with the message op code, and continuing with the rest of the bytes in the data (with the exception of the CRC itself that is being calculated). Of course, in other embodiments, the CRC calculations may use the telemetry ID of the originator at a point other than at the beginning of the calculation. In still other embodiments, the Op-Code may be left out of the CRC calculation. In still other embodiments, the order in which the components of the messages are calculated may be changed, though if different from the order presented in the message itself, recalculation of the CRC by the receiver may not be able to be performed on the fly as the message is being received as is done in the current embodiment.

Some messages must be transferred with very high levels of reliability, while other messages are not as critical. As such, various levels of information may be communicated so that various levels of error checking may occur. In the present embodiment, all transmissions include some type of error check code where more critical messages are provided with a more secure code. In the present embodiment, multiple levels of security have been defined. In particular, three levels of security have been established though in other embodiments fewer or greater numbers of levels may be used. In the present embodiment, the three levels of security or criticality are (1) status, (2) command, and (3) critical.

Status messages are the least critical and they are transmitted with a one byte CRC code. Periodic status updates and response messages are examples of this message type.

Command messages are of intermediate criticality and are transmitted with a 16-bit CRC code.

Critical messages are of the highest criticality and are subjected to the highest level of security. These messages are used to establish insulin delivery. Critical messages are transmitted with a 16-bit CRC and are also transmitted with duplicate data in the data portion of the message. The receiver verifies that both copies of the data are identical before using the message. Furthermore, various delivery amounts indicated in the messages will be compared to various predefined maximum amounts to confirm that they are within reasonable limits.

In the present embodiment, the 16-bit CRC is based on the CCITT polynomial $x17+x12+x5+1$ as described in The CCITT Red Book", Volume VIII, published by International Telecommunications Union, Geneva, 1986, Recommendation V.41, "Code-Independent Error Control System". This book is hereby incorporated by reference herein as if set forth in full. The 8-bit CRC polynomial used for other messages in the present embodiment is based on the polynomial $x8+x5+x4+1$.

Further details about CRCs and CRC calculation are provided in a book entitled "C Programmer's Guide to Serial Communications", 2nd Edition, by Joe Campbell, published by SAMS Publishing, Indianapolis, Ind., ISBN 0-672-30286-1. In particular chapter 3 deals with Errors and Error Detection including CRCs, while chapter 23 deals with calculation of CRCs. This book is hereby incorporated by reference herein as if set forth in full.

A "C" language program for generating a 16-bit CRC lookup table is set forth in FIG. 4. The table generated by this program is used in the creation of 16-bit CRC of a data stream as well as in the verification of that data stream after its transmission and reception. The table generated by this program matches the table set forth on page 775 of the above noted CCITT Red Book reference.

Using the table generated using the above program, or using some other 16-bit CRC table, in combination with the process discussed hereafter a 16 bit CRC for a data stream may be obtained. The CRC starts with a 16-bit value of 0x0000 or with some other value that is predefined. The starting value of the CRC may be considered as the CRC Key and may be derived from any appropriate data string such as that of the telemetry ID for the transmitter. Each time a byte of the data stream (D_BYTE) is processed a new, or accumulated, CRC value (CRC_ACC) is derived. The CRC_ACC that is thus determined is modified and the modified CRC in conjunction with the next byte of data is used to derive a next CRC_ACC value.

A process for deriving a final CRC value for a data stream may involve several steps:

A. Start with a 16 bit CRC_ACC value equal to 0x0000 or to some other value defined by a key.

B. Derive an index (i.e. T_IND) to the CRC table by taking the high byte (i.e. HB) of the present value of the CRC_ACC and performing an Exclusive-OR (i.e. XOR) between it and the current D_Byte, bit-by-bit. The 8 bit value resulting from this exclusive OR operation is the index to the 16 bit CRC table. This may be more concisely expressed as, $$T\_IND=(HB \text{ of } CRC\_ACC) XOR (D\_Byte)$$

C. Next, replace CRC_ACC by shifting its low byte (i.e. LB) to its high byte and inserting a new low byte containing all zeros. This may be alternatively expressed as, $$CRC\_ACC(HB)=CRC\_ACC(LB)$$

$$CRC\_ACC(LB)=00 \text{ hex}$$

$$CRC\_ACC=CRC\_ACC(HB)+CRC\_ACC(LB),$$

where "+" is used to represent the joining of the high byte and the low byte into a single sixteen bit entity.

D. Next, the new value of the CRC_ACC is determined by pulling a 16 bit value from the Table (CRC_TAB) using the table index (T_IND) derived in step B and performing an XOR operation between it and the existing CRC_ACC. This may be more concisely expressed as, $$CRC\_ACC = (CRC\_ACC)XOR(CRC\_TAB[T\_IND]).$$

E. Next, the process loops back through steps (B.)–(D.) until the last byte in the data stream has been processed and the final CRC_ACC value is determined.

F. The resultant 16-bit CRC (CRC_ACC) is appended to the end of the data stream with the High Byte followed by the Low Byte.

The C-language program set forth in FIG. 5 may be used to generate an 8-bit CRC lookup table. The created table may be used to create and verify the 8-bit CRC of a data stream.

The following process may be used, in conjunction with the table created by the above program, or in conjunction with some other 8 bit CRC table, to create an 8 bit CRC for a given data stream. The CRC starts with an 8 bit value of 0x00 or with some other value that is predefined. The starting value of the CRC may be considered as the CRC Key. Each time a byte of the data stream (D_BYTE) is processed, a new or accumulated, CRC value (CRC_ACC) is derived. The CRC_ACC thus determined is then used in conjunction with the next byte of data to derive a next CRC_ACC.

A process for deriving a final CRC value for a data stream may involve several steps:

A. Start with an 8 bit CRC_ACC value equal to 0x0000 or to some other value defined by a key.

B. Derive an index (i.e. T_IND) to the CRC table by taking the present value of the CRC_ACC and performing an Exclusive-OR (i.e. XOR) between it and the current D_Byte, bit-by-bit. The 8 bit value resulting from this exclusive OR operation is the index to the CRC table. This may be more concisely expressed as, $$T\_IND = (CRC\_ACC)XOR(D\_Byte).$$

C. Next, the new value of the CRC_ACC is determined by pulling the 8-bit value from the Table (CRC_TAB) using the table index (T_IND) derived in step B. This may be more alternatively expressed as, $$CRC\_ACC = CRC\_TAB[T\_IND].$$

D. Next, the process continues to loop through steps (B) and (C) until the last byte in the data stream has been processed and the final CRC_ACC value is determined.

E. The resultant 8-bit CRC (CRC_ACC) is appended to the end of the data.

The receiver of the data stream, with the CRC code appended to its end, calculates the CRC byte-by-byte, just as the transmitter did originally, based on the data stream received. If the receiver does not include the transmitted CRC in the calculation (e.g. the last two bytes received in the case of a 16 bit CRC, or the last byte in the case of an 8 bit CRC), the CRC value calculated may be compared to the CRC value received and if they match, the receiver may conclude that the data transmitted is identical to the data received. If the codes do not match, the data stream must be rejected.

Alternatively, if the receiver calculates the CRC using the data stream that includes the transmitted CRC (e.g. the last two bytes for a 16 bit CRC or the last one byte for an 8 bit CRC), the CRC value calculated will be zero if the transmitted data and the received data are identical. As such if the result of the calculation is not zero, the receiver must reject the data stream.

If it is desired that a portion of the data be randomized for-transmission, a modification to the CRC calculation process may be implemented to provide such randomization. It may be desirable to randomize the data (may be more descriptively stated as pseudo-randomization of the data) so that bit transitions will occur regularly in order to ensure that bit synchronization is maintained between the transmitted data and the receiver of the data. An advantage to the randomization process of this embodiment, is that the randomization may occur on the fly in a single pass, byte-by-byte, as the data is being prepared for transmission. A further advantage is that the message length remains constant. Similarly, upon receipt of the data, the receiver may de-randomize the data on the fly in a single pass, as it is being received with the use of a single extra 8-bit variable.

The randomization process can be implemented by adding a step (D'.) between steps (D.) and (E.) as presented above for the 16-Bit CRC Derivation.

D'. After processing the current byte and deriving the new CRC based on the inclusion of that byte in the data string. Redefine the next byte (D_BYTE) in the data string to be the 8-bit value obtained from the XOR of the Original Value of the Next Data Byte (D_BYTE) with either the least significant byte (LS_BYTE) or the most significant byte (MS_BYTE) of the CRC Table Value (CRC_TAB) used in processing the current data byte, (i.e. what was used in step (D.)), as derived using Table Index (T_IND) derived in step B. It doesn't matter whether the LS_BYTE or the MS_BYTE is used so long as it is used consistently. This may be more concisely stated as, $$(D\_BYTE) = (D\_BYTE)XOR(CRC\_TAB[T\_IND]).$$

This newly defined D_Byte (modified, or randomized, version of the next data byte in the data stream) is used when looping back to step (B.). In the present embodiment, as this step is added before looping back to step (B.), the first, or initial byte does not undergo this process and is thus not randomized.

In addition to calculating a 16-bit CRC (as described above) based on data that has been received, if the data has been randomized, an additional three steps may be taken in the data recovery process to unrandomize the data and verify its accurate reception.

These three steps are inserted following the CRC calculation for a given byte. In other words these three steps come between steps (D.) and (E.) and are hereafter presented as steps (D'.), (D".), and (D'".).

D'. If the data byte used in steps (B.)–(D.) was not the first, or initial, data byte, then define the value of the data byte (D_BYTE) as the value of a data byte restoration variable (D_BYTE_RES) that was obtained when processing the previous data byte as is defined below. This may alternatively be expressed as (If not Initial Data Byte)$D\_BYTE = D\_BYTE\_RES.$ D". Process or retain D_BYTE as the unrandomized byte of data to be used for further processing once the CRC calculation and any other checks confirm that the message was properly transmitted and received.

D'". Next derive a new value for the data byte restoration variable as the result of an XOR operation between the next data byte (N_D_BYTE) transmitted in the stream and either the MS byte or the LS byte, which ever was used to perform randomization when the data was prepared for transmission, of the CRC Table Value (CRC_TAB) used in processing the current data byte, (i.e. what was used in step (D.)), as derived using Table Index (T_IND) derived in step (B.) from processing the previous data byte in the stream. This may be more concisely expressed as,

D_BTYE_RES=(N_D_BYTE)XOR(CRC_TAB[T_IND]).

The algorithms set forth above may be applied in the present system by via software programming, firmware programming, or hardware configuration. The preferred implementation makes use of a computer (processor) programmed via software to carry out the algorithm.

Figure 6A:
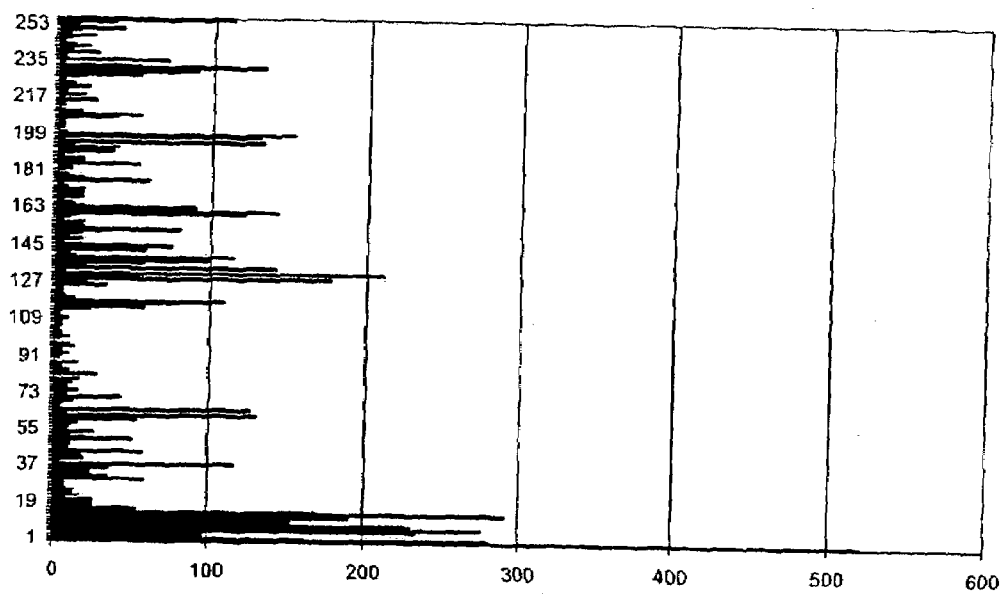
FIGS. 6a and 6b depict bar charts that illustrate the difference in byte pattern distributions before and after randomization.
Figure 6B:
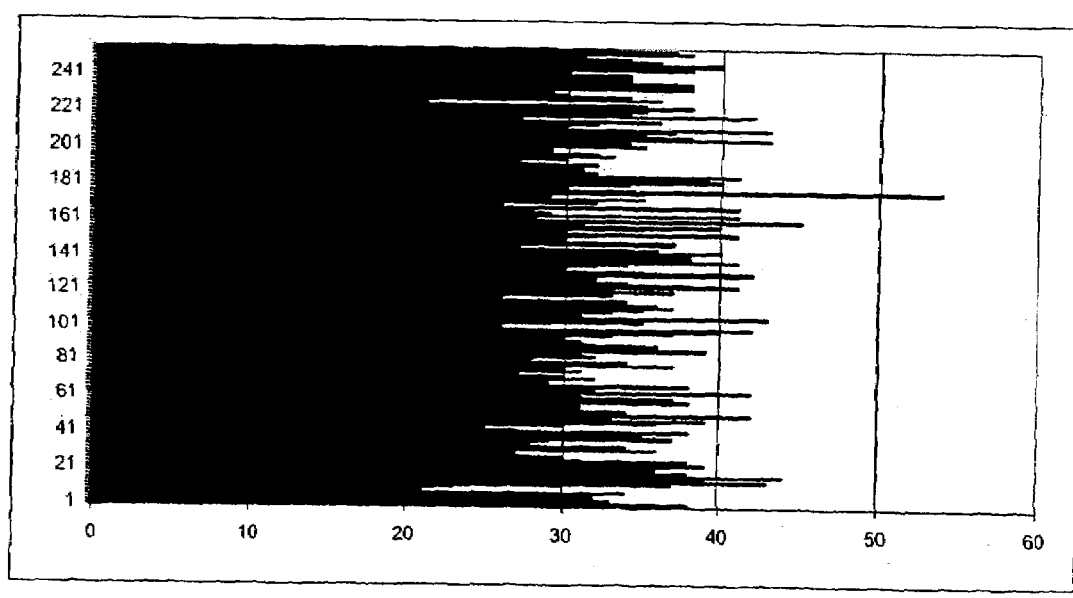

An example of the enhancement offered by data randomization, and in particular by the randomization scheme set forth above, is illustrated in FIGS. 6a and 6b. FIG. 6a provides a bar chart illustrating byte pattern distributions (hex values 0x00 to 0xFF) for 8196 bytes of typical data that might be downloaded into an implantable pump. As can be seen in the figure a number of byte distributions are seen 200+ times in data while many byte distributions are seen fewer than 25 times. FIG. 6b provides a bar chart illustrating the byte pattern distributions of the data of FIG. 6a after it been randomized according to the above algorithm. As can be seen in the figure most byte distributions are seen in the range of 30 to 40 times with only few being seen less than 20 and more than 40 times. It may be concluded from FIGS. 6a and 6b the randomization process has lead to a more uniform distribution of byte pattern values. It may also be concluded that the data will have a more uniform distribution of transitions and an increased number of transitions.

An increase in the number of bit transitions after modification than before modification may be understood by first considering the number of bit transitions in the data prior to modification (e.g. randomization), or a selected portion of the data, that is to be transmitted via telemetry, and then comparing that number to the number of transitions that exist in the data after modification has been made.

A decrease in the maximum spacing between bit transitions after modification (e.g. randomization) may be understood by first analyzing the data prior to modification and determining the maximum number of bits between two consecutive transitions and then performing a similar analysis after modification, and comparing the two maximum values to determine whether a decrease occurred.

A more uniform spacing of bit transitions in the data, or a selected portion of the data, after modification (e.g. randomization) than in the corresponding data prior to modification, may be understood by first analyzing the data prior to modification and determining the average number of bits between transitions and the standard deviation, or the like, and then performing a similar analysis after modification and determining if the standard deviation has decreased (i.e. an increase in uniformity of the transitions).

A more uniform distribution of byte patterns after modification (e.g. randomization) may be understood by determining the average number of times each of the 256 potential bit patterns for each byte (i.e. byte patterns) exists in the data prior to modification, or in a selected portion of the data to be transmitted, and determining the standard deviation associated with this average and then making a similar determination after modification and comparing the standard deviations to determine if a decrease has occurred after modification (i.e. a more uniform distribution of byte patterns).

An analogous algorithm may be defined for randomizing and de-randomizing the data associated with an 8-bit CRC value.

The above CRC coding and randomization technique may be used in the transmission and reception of data to and from the implantable device and the external communication device. Furthermore, this technique may be used when transmitting data to and from the external communication device and a second external communication device using either RF telemetry, the IR communication link, or some other communication link (e.g. other electromagnetic frequency range such as visible radiation). The above CRC and randomization algorithm may be implemented in hardware, software, or a combination thereof.

In the preferred embodiment, instead of using a 0000x0 value as the key, it is preferred that the sender's telemetry ID be used in generating a key. Such keying will cause the receiver to reject any messages that it receives (even if its telemetry ID is used to direct the transmission) if it does not use the sender's telemetry ID in computing the CRC or in de-randomizing the data portion of the message. In the first preferred embodiment the sender's telemetry ID is not explicitly set forth in the message but acts as a hidden piece of data that must be pre-known to successively receive the message. In alternative embodiments the sender's telemetry ID may be explicitly set forth in the message.

Though the randomization process may be used in conjunction with any messages that are transmitted between the implanted device and the external communication device, the randomization process may be limited to use with messages having a certain minimum size, such as having data portions that are at least 5, 10, or 15 bytes in length. This may be implemented by adding an additional step in the algorithm to compare the anticipated message size to the minimum size. Alternatively, the randomization algorithm may be the default implementation and a check is performed based on anticipated maximum message size to determine whether to deactivate the default randomization. Alternatively, only messages having certain op-codes or data associated with a certain minimum level of criticality (e.g. carrying a 16 bit CRC) may be subject to randomization. In other alternatives, other portions of the message may be subject to randomization besides the data. In still other alternatives randomization may be applied only to messages originating from a selected one of the implantable device or external communication device.

In an alternative embodiment, the randomization technique discussed above may be used with another randomization source. The other source may be set forth in a table or derived by calculation. In still further alternatives, the de-randomization need not occur in a single pass through the incoming data though a single pass derandomization is more preferable.

Various alternative approaches to CRC derivation are possible and will be apparent to those of skill in the art upon review of the teachings provided herein.

Various alternative approaches to data randomization and de-randomization are possible and will be apparent to those of skill in the art upon review of the teachings provided herein. For example, a pseudo-random number generator with a randomization sequence number embedded in the message could be used.

The most preferred randomization schemes will not lead to expansion of the message length while the most preferred de-randomization schemes will cause data recovery to occur in a single pass through the data. However, in alternative embodiments, the message lengths may be expanded (e.g.

by adding in a predefined periodic extra bit or bits) and de-randomization may take more than one pass through the data for complete message recovery to occur.

The added data may take the form of a single bit of data that is added to the message. It may take the form of multiple bits of data added as group to a single location in the message. Alternatively, it may take the form of a single or multiple bits added on a periodic basis to a message or at least to a certain portion of a message. The adding of the bits to the message will occur in a manner that can be decoded by the receiver so that the intended information may be distinguished from the extraneous information. The adding of the segments of information (i.e. single bits or multiple bits) may occur based on fixed intervals and a predefined trigger for starting the insertion. The adding may occur based on attributes of the data pattern that is to convey the information. Such attributes might involve recognition that a certain number of bits exist consecutively that do not contain a transition and as such a bit or bits may be added after the certain number. The added bit or bits may be based on the value of the certain number of bits that did not transition. For example if the certain number is set to 50, after transmission of the 50 bits of identical value, one bit may be added that has an opposite value to that of the 50. As another example, if bits are to be inserted on a fixed basis regardless of the bit values in the transmitted data, single bits may be added to selected locations where every other added bit has the opposite value to the last. Alternatively, pairs of opposite valued bits may form each insertion.

Figure 7:
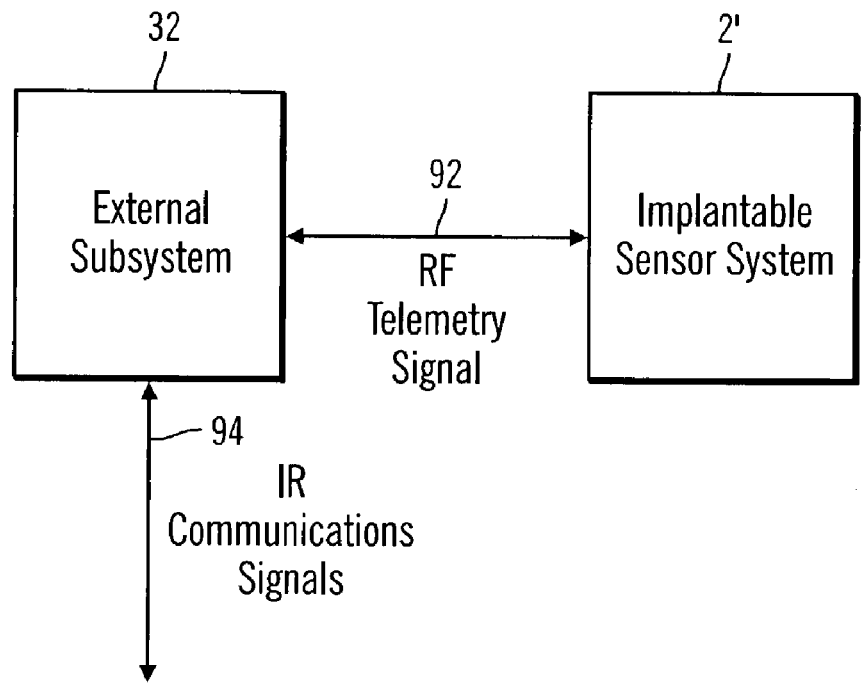
FIG. 7 depicts a block diagram of an implantable sensor and an external communication device, according to embodiments of the present invention.
Figure 8:
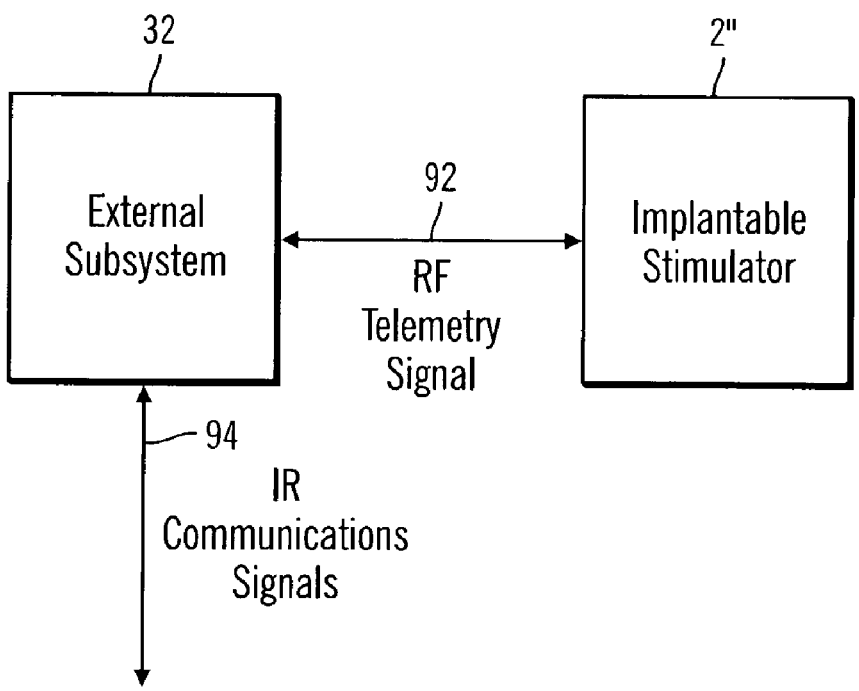
FIG. 8 depicts a block diagram of an implantable stimulator and an external communication device, according to embodiments of the present invention.

In alternative embodiments, the medical device may be any of an implantable sensor system 2' (e.g. an electrochemical sensor such as an oxygen or a glucose sensor (see FIG. 7), an implantable stimulator 2" (e.g. a pacemaker, defibrillator, nerve stimulator) (see FIG. 8) or an external ambulatory device (e.g. an external pump with a transcutaneous catheter for infusing insulin or other desired drug, or an electrochemical glucose sensor or optical glucose sensor located within the patient's body via a transcutaneous lead.) In these various alternatives, the physical, electronic, and programmed features of the communication device and implantable device have different components and features than presented above for the implantable pump so that their desired medical functionality and safety requirements are achieved and such that appropriate control and feedback is provided within the communication device.

Various the features of the above embodiment and its alternatives provide enhanced ability to transmit and receive messages so that communication can occur with enhanced efficiency and little inconvenience to the user as need for repeated transmission is reduced while message length is not increased or not substantially increased. These improvements provide more robust, effective, reliable, and safe operation of an implantable medical device and more generically for an ambulatory medical device.

While the above embodiment has primarily been concerned with an implantable infusion pump that dispenses insulin using a piston type pump mechanism, the telemetry and timing features disclosed herein may be used in other ambulatory devices such as implantable pacemakers, defibrillators, other implantable tissue stimulators, implantable physiologic sensors such as electrochemical oxygen sensors, peroxide sensors, or enzymatic sensors such as glucose sensors, externally carried infusion pumps, implantable infusion pumps that use other pumping mechanisms or simply used excess pressure and controlled flow elements to infuse various medications and drugs such as analgesics, drugs for treating AIDS, drugs for treating psychological disorders and the like. For example, the telemetry features presented above may be used with an external infusion pump that may or may not have a built in display and keypad but is equipped with a telemetry system that can communicate with a physically separated communication device so that the pump need not be accessed in order to provide commands to it and receive data from it.

In these various alternatives, the physical, electronic, and programmed features of the communication device and implantable device may have different components and features than presented above for the implantable pump system so that their desired medical functionality and safety requirements are achieved and such that appropriate control and feedback is provided between the medical device and its communication device.

In other alternative embodiments the medical device may include two medical devices such as an implantable pump and an implantable sensor. The pump may dispense a drug whose physiological impact on the body (e.g. analgesic impact) is ascertained by the sensor or alternatively the sensor may supply a physiological reading that indicates a need for infusion of the drug. The pump may operate in a closed loop manner with the sensor or it may operate in an open loop manner where the patient is required to interpret sensor output information and is required to issue appropriate infusion commands to the pump. For example, in the case of a diabetic patient, the drug may be insulin and the sensor may detect glucose level.

In other alternative embodiments two medical devices may be implanted adjacent one another or at an extended distance from one another. If not placed in physical contact with one another, a lead may be used to provide power conduction from one device to the other and also be used to conduct communication signals between the devices. Alternatively, each device may include at least one telemetry system that allows direct communication between each or allows indirect communication to occur via the external communication device or other external device. Each device may be supplied with its own power supply. Depending on the communication requirements each device may use two way communication (i.e. both outbound and inbound communication) or allow only one way communication (i.e. outbound communication or possibly inbound communication).

In other alternatives, both the medical device and the communication device may be external devices (e.g. an external pump and an external RF telemetry based communication device). In still further alternatives, a first type of medical device may be implanted (e.g. an infusion pump or a sensor) while a second medical device may be external (e.g. the opposite of a sensor or an infusion pump). Where at least one of the medical devices is external, it may also function as the communication device for the other medical device in which case it may possess a display for providing information to the patient and a keypad for allowing entry of commands for issuance to the implantable device as well as for direct use by itself. Even if at least one of the medical devices is external, it may be inconvenient to access that device when information is needed or commands must be given, as such an external, non-medical communication device may be supplied that has information output (e.g. display) capabilities and input (e.g. keypad) capabilities. If a separate communication device is provided, the external medical device may or may not have display and input capabilities.

The telemetry features presented above may be used with various forms of distant communication (e.g. between the implantable device and other external devices or between the external communication device and other external devices). For example communication may occur via various electromagnetic links like IR, optical links, longer or shorter wavelength RF, audio links, ultrasonic links, acoustic links, inductive links, and the like. Various telemetry systems may be used. Telemetry systems may be of the analog type, digital type, or mixed.

The various telemetry and timing features presented above may be used in various combinations be used separately to enhance communications between ambulatory medical devices and communication devices and/or controllers associated therewith.

In other embodiments two independent processors may be used that operate from a single timing chain. In these alternatives, it is preferable that at least one of the timing signals (e.g. one of the lower frequency timers) be monitored by an independently timed watchdog circuit to reduce the risk of timing problems going undetected.

In still additional embodiments, an implantable glucose sensor may be used in conjunction with an implantable insulin pump to provide feedback to the patient or physician on the effectiveness of the insulin delivery system. The patient could use the feedback to assist in making insulin delivery decisions in an open loop manner. Alternatively, the operation of the pump could be tied to the sensor output in a more or less closed loop manner to give a more automated character to system operation. Insulin may be infused without any user intervention, without pre-delivery information, and even without direct post delivery feedback. In a less automated closed loop system, drug infusion recommendations could be derived by the system and presented to the user before delivery or the system could require user acknowledgment prior to proceeding with delivery for amounts or rates exceed a predefined limit. The implantable sensor may have its own power supply or may receive power from the control circuitry provided within the pump housing through a physical lead that connects them. Power may be supplied through one or more independent leads or alternatively may be transferred over one or more data lines through the communication signals themselves. Communication may be exchanged in various ways including, for example, via galvanic leads, RF telemetry, fiber optics, and the like, and may be of digital, analog, or combined form. The sensor system may include a plurality of sensor elements which might allow continued glucose data to be supplied even though some portion of the sensors stop operating, lose calibration or produce questionable readings. The most preferred sensors would include electronic processing capability in the form of an integrated circuit mounted in or forming a part of a housing for the sensor. This configuration has the advantage of allowing digital communications between the physical sensor and any separated electronic control module.

Further teachings concerning implantable sensors and implantable sensor systems are found in a number of patents issued to D. A. Gough, including (1) U.S. Pat. No. 4,484,987, entitled "Method And Membrane Applicable To Implantable Sensors", (2) U.S. Pat. No. 4,627,906, entitled "Electrochemical Sensor Having Improved Stability"; (3) U.S. Pat. No. 4,671,288, entitled "Electrochemical Cell Sensor For Continuous Short-Term Use In Tissues And Blood"; (4) U.S. Pat. No. 4,703,756, entitled "Complete Glucose Monitoring System With An Implantable Telemetered Sensor Module"; and (5) U.S. Pat. No. 4,781,798, entitled "Transparent Multi-Oxygen Sensor Array And Method Of Using Same". Each of these patents is incorporated herein by reference as if set forth in full.

Still further teachings concerning implantable sensors and sensor systems are found in a number of patents issued to J. H. Schulman, et al., including (1) U.S. Pat. No. 5,497,772, entitled "Glucose Monitoring System"; (2) U.S. Pat. No. 5,651,767, entitled "Replaceable Catheter System for Physiological Sensors, Stimulating Electrodes and/or Implantable Fluid Delivery Systems"; (3) U.S. Pat. No. 5,750,926, entitled "Hermetically Sealed Electrical Feedthrough For Use With Implantable Electronic Devices"; (4) U.S. Pat. No. 6,043,437, entitled "Alumina Insulation for Coating Implantable Components and Other Microminiature Devices"; (5) U.S. Pat. No. 6,088,608, entitled "Implantable Sensor and Integrity Test Therefor"; and (6) U.S. Pat. No. 6,119,028, entitled "Implantable Enzyme-Based Monitoring Systems Having Improved Longevity Due to Improved Exterior Surfaces". Each of these patents is incorporated herein by reference as if set forth in full.

Additional further teachings concerning implantable sensors and sensor systems are found in (1) U.S. Pat. No. 5,917,346, issued to J. C. Gord, et al., and entitled "Low power current-to-frequency converter"; (2) U.S. Pat. No. 5,999,848, issued to J. C. Gord, and entitled "Daisy Chainable Sensors for Implantation in Living Tissue"; (3) U.S. Pat. No. 5,999,849, issued to L. D. Canfield, et al., and entitled "Low Power Rectifier Circuit for Implantable Medical Devices"; and (4) U.S. Pat. No. 6,081,736, issued to M. S. Colvin, et al., and entitled "Implantable Enzyme-Based Monitoring Systems Adapted for Long Term Use". Each of these patents is incorporated herein by reference as if set forth in full.

Further teachings concerning implantable infusion pumps are found in a number of patents by R. E. Fischell, including (1) U.S. Pat. No. 4,373,527, entitled "Implantable, Programmable Medication Infusion System"; (2) U.S. Pat. No. 4,494,950, entitled "Infusion Device Intended for Implantation in a Living Body"; (3) U.S. Pat. No. 4,525,165, entitled "Fluid Handling System for Medication Infusion System"; (4) U.S. Pat. No. 4,573,994, entitled "Refillable Medication Infusion Apparatus"; (5) U.S. Pat. No. 4,594,058, entitled "Single Valve Diaphragm Pump with Decreased Sensitivity to Ambient Conditions"; (6) U.S. Pat. No. 4,619,653, entitled "Apparatus For Detecting At Least One Predetermined Condition And Providing An Informational Signal In Response Thereto In A Medication Infusion System"; (7) U.S. Pat. No. 4,661,097, entitled "Method for Clearing a Gas Bubble From a Positive Displacement Pump Contained Within a Fluid Dispensing System"; (8) U.S. Pat. No. 4,731,051, entitled "Programmable Control Means for Providing Safe and Controlled Medication Infusion"; and (9) U.S. Pat. No. 4,784,645, entitled, "Apparatus For Detecting A Condition Of A Medication Infusion System And Providing An Informational Signal In Response Thereto". Each of these patents is incorporated herein by reference as if set forth in full.

Still further teachings concerning infusion pumps are found in a number of patents by Franetzki, including (1) U.S. Pat. No. 4,191,181, entitled "Apparatus For Infusion of Liquids", (2) U.S. Pat. No. 4,217,894, entitled "Apparatus for Supplying Medication to the Human or Animal Body"; (3) U.S. Pat. No. 4,270,532, entitled "Device for the Pre-programmable Infusion of Liquids"; (4) U.S. Pat. No. 4,282,872, entitled "Device for the Pre-programmable Infusion of Liquids", U.S. Pat. No. 4,373,527, entitled "Implantable, Programmable Medication Infusion System"; (5) U.S. Pat. No. 4,511,355, entitled "Plural Module Medication Delivery System", (6) U.S. Pat. No. 4,559,037, entitled "Device for the Pre-programmable Infusion of Liquids"; (7) U.S. Pat. No. 4,776,842, entitled "Device for the Administration of Medications". Each of these patents is incorporated herein by reference as if set forth in full.

Teachings concerning tissue stimulators are found in a number of patents by J. H. Schulman, including (1) U.S. Pat. No. 5,193,539, entitled "Implantable microstimulator"; (2) U.S. Pat. No. 5,193,540; entitled "Structure and Method of Manufacture of an Implantable Microstimulator"; and (3) U.S. Pat. No. 5,358,514, entitled "Implantable Microdevices with Self Attaching Electrodes". Further teachings are also found in (1) U.S. Pat. No. 5,957,958, by Loeb et al., entitled "Implantable nerve or muscle stimulator e.g. a cochlear prosthesis", in (2) U.S. Pat. No. 5,571,148, by G. E. Loeb, et al., entitled "Implantable Multichannel Stimulator"; and in (3) PCT Publication No. WO 00/74751, by A. E. Mann, and entitled "Method and Apparatus for Infusing Liquids Using a Chemical Reaction in an Implanted Infusion Device". Each of these publications is incorporated herein by reference as if set forth in full.

The control of an implantable sensor could be provided through the functionality of one or both processor ICs. One processor IC could supply power and/or control signals to the sensor(s) and receive data back from the sensor, while the other processor could monitor the activity to ensure that sensor activity meets certain predefined guidelines.

In other embodiments, the external communication device of the first embodiment could be functionally linked to an external glucose sensor system such as the continuous glucose monitoring system (CGMS) offered by Minimed Inc. of Northridge, Calif. The link may be established, for example, through a physical lead or by RF telemetry.

In other embodiments other implantable, or external, sensor systems that measure something other than glucose could also be functionally coupled to the implantable device either to receive power and/or to provide data. Other such sensors might include oxygen sensors, peroxide sensors, pulse rate sensors, temperature sensors, accelerometers, and the like.

In still other alternative embodiments, the electronic control system of the first embodiment could be configured to control one or more implantable sensors or electrical stimulators with or without infusion functionality incorporated into the implantable device.

Further embodiments will be apparent to those of skill in the art upon review of the disclosure provided herein. Still further embodiments may be derived from the teachings set forth explicitly herein in combination with the teachings found in the various patent applications.

While the description herein sets forth particular embodiments, it is believed that those of skill in the art will recognize many variations to the presented embodiments based on the teachings herein, as such it is believed that many additional modifications may be made without departing from the spirit of the teachings herein. The accompanying claims are intended to cover such modifications as would fall within the true scope and spirit of the present invention.

The disclosed embodiments are therefore to be considered as illustrative and not necessarily restrictive, the scope of the invention being indicated by the appended claims, rather than the foregoing description, and all changes which come within the meaning and range of equivalency of the claims are therefore intended to be embraced therein

We claim:

1. A method of communicating between medical system components, comprising:
   providing an ambulatory medical device (MD) for treating or monitoring a selective state of a body of a patient, the ambulatory medical device having an MD electronic control circuitry with at least one MD telemetry system and at least one MD processor;
   controlling, with the MD processor, at least part of the operation of the MD telemetry system and of the ambulatory medical device;
   providing a communication device (CD) for sending messages to or receiving messages from the MD telemetry system, the communications device having CD electronic control circuitry with at least one CD telemetry system and at least one CD processor;
   controlling, with the CD processor, at least part of the operation of the CD telemetry system and of the communication device; and
   modifying at least one portion, but not all, of at least one message with at least one of the MD processor and the CD processor, in preparation for transmission by the medical device or the communication device such that a higher number of bit transitions occur in the at least one modified portion than were found in corresponding at least one portions prior to being modified.

2. The method of claim 1 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

3. The method of claim 1 wherein the at least one modified portion of the at least one message includes no more bits than found in the corresponding at least one portions prior to being modified.

4. The method of claim 3, wherein modifying the at least one portion comprises providing a pseudo-randomization of the at least portion.

5. The method of claim 4 wherein the pseudo-randomization occurs in a single pass as the message is being prepared for transmission by one of the medical device or the external communication device.

6. The method of claim 5 wherein a de-randomization occurs in a single pass as the message is being received by the other of the external communication device or the medical device.

7. The method of claim 6 wherein the pseudo-randomization is obtained by use of a CRC table.

8. The method of claim 7, further comprising
   preparing an error checking code using the CRC table; and
   transmitting the error checking code with the message.

9. The method of claim 7 wherein the at least one message comprises an identifier of the receiver or the transmitter, an op-code, and data, wherein the identifier and op-code are not randomized but the data is randomized.

10. The method of claim 3 wherein the medical device comprises an implantable medical device.

11. The method of claim 10 wherein the medical device comprises at least one of (1) an implantable infusion pump for selectively dispensing a selected drug, (2) an implantable infusion pump for selectively dispensing insulin, (3) an implantable sensor for sensing a selected state of the body, (4) an implantable sensor for sensing glucose level, or (5) an implantable electrode for selectively stimulating a portion of the body of the patient.

12. The method of claim 1 wherein:
the at least one message comprises a plurality of elements; and
the modifying at least one portion, but not all, of at least one message comprises modifying at least one element of the at least one message, but not all elements of the at least one message.

13. The method of claim 12 wherein:
the at least one message comprises at least one data element, and at least one of a preamble element, a frame sync element, and an identifier element of the transmitter or the receiver; and
the modifying at least one portion, but not all, of at least one message comprises modifying at least one data element of at least one message.

14. A method of communicating between medical system components, comprising:
providing an ambulatory medical device (MD) for treating or monitoring a selective state of a body of a patient, the ambulatory medical device having an MD electronic control circuitry with at least one MD telemetry system and at least one MD processor;
controlling, with the MD processor, at least part of the operation of the MD telemetry system and of the ambulatory medical device;
providing a communication device (CD) for sending messages to or receiving messages from the MD telemetry system, the communications device having CD electronic control circuitry with at least one CD telemetry system and at least one CD processor;
controlling, with the CD processor, at least part of the operation of the CD telemetry system and of the communication device; and
modifying at least one portion, but not all, of at least one message with at least one of the MD processor and the CD processor, in preparation for transmission by the medical device or the communication device such that a more uniform spacing of bit transitions exist in the at least one modified portion than were found in corresponding at least one portion prior to being modified.

15. The method of claim 14 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

16. The method of claim 14 wherein the medical device comprises an implantable medical device.

17. The method of claim 14 wherein the medical device comprises at least one of (1) an implantable infusion pump for selectively dispensing a selected drug, (2) an implantable infusion pump for selectively dispensing insulin, (3) an implantable sensor for sensing a selected state of the body, (4) an implantable sensor for sensing glucose level, or (5) an implantable electrode for selectively stimulating a portion of the body of the patient.

18. The method of claim 14 wherein:
the at least one message comprises a plurality of elements; and
the modifying at least one portion, but not all, of at least one message comprises modifying at least one element of the at least one message, but not all elements of the at least one message.

19. The method of claim 18 wherein:
the at least one message comprises at least one data element, and at least one of a preamble element, a frame sync element, and an identifier element of the transmitter or the receiver; and
the modifying at least one portion, but not all, of at least one message comprises modifying at least one data element of at least one message.

20. The method of claim 19, wherein:
modifying the at least one portion comprises providing a pseudo-randomization of the at least one portion; and
the pseudo-randomization is obtained by use of a CRC table.

21. The method of claim 20, further comprising
preparing an error checking code using the CRC table; and
transmitting the error checking code with the message.

22. The method of claim 20 wherein the at least one message comprises an identifier of the receiver or the transmitter, an op-code, and data, wherein the identifier and op-code are not randomized but the data is randomized.

23. A method of communicating between medical system components, comprising:
providing an ambulatory medical device (MD) for treating or monitoring a selective state of a body of a patient, the ambulatory medical device having an MD electronic control circuitry with at least one MD telemetry system and at least one MD processor;
controlling, with the MD processor, at least part of the operation of the MD telemetry system and of the ambulatory medical device;
providing a communication device (CD) for sending messages to or receiving messages from the MD telemetry system, the communications device having CD electronic control circuitry with at least one CD telemetry system and at least one CD processor;
controlling, with the CD processor, at least part of the operation of the CD telemetry system and of the communication device; and
modifying at least one portion, but not all, of at least one message with at least one of the MD processor and the CD processor, in preparation for transmission by the medical device or the communication device such that a more uniform distribution of byte patterns occur in the at least one modified transmitted message than in the corresponding at least one portion prior to being modified.

24. The method of claim 23 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

25. The method of claim 23 wherein the medical device comprises an implantable medical device.

26. The method of claim 23 wherein the medical device comprises at least one of (1) an implantable infusion pump for selectively dispensing a selected drug, (2) an implantable infusion pump for selectively dispensing insulin, (3) an implantable sensor for sensing a selected state of the body, (4) an implantable sensor for sensing glucose level, or (5) an implantable electrode for selectively stimulating a portion of the body of the patient.

27. The method of claim 23 wherein:
the at least one message comprises a plurality of elements; and the modifying at least one portion, but not all, of at least one message comprises modifying at least one element of the at least one message, but not all elements of the at least one message.

28. The method of claim 27 wherein:

the at least one message comprises at least one data element, and at least one of a preamble element, a frame sync element, and an identifier element of the transmitter or the receiver; and the modifying at least one portion, but not all, of at least one message comprises modifying at least one data element of at least one message.

29. The method of claim 28, wherein:

modifying the at least one portion comprises providing a pseudo-randomization of the at least one portion; and the pseudo-randomization is obtained by use of a CRC table.

30. The method of claim 29, further comprising preparing an error checking code using the CRC table; and transmitting the error checking code with the message.

31. The method of claim 29 wherein the at least one message comprises an identifier of the receiver or the transmitter, an op-code, and data, wherein the identifier and op-code are not randomized but the data is randomized.

32. A process of communicating between medical system components, comprising:

providing an ambulatory medical device (MD) for treating or monitoring a selective state of a body of a patient, the ambulatory medical device having an MD electronic control circuitry with at least one MD telemetry system and at least one MD processor;

controlling, with the MD processor, at least part of the operation of the MD telemetry system and of the ambulatory medical device;

providing a communication device (CD) for sending messages to or receiving messages from the MD telemetry system, the communications device having CD electronic control circuitry with at least one CD telemetry system and at least one CD processor;

controlling, with the CD processor, at least part of the operation of the CD telemetry system and of the communication device; and modifying at least one portion, but not all, of at least one message by a randomization algorithm in preparation for transmission from a first of the medical device or the communication device to a second of the communication device or the medical device, such that a higher number of bit transitions occur in the at least one modified portion than were found in corresponding at least one portion prior to being modified.

33. The method of claim 32 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

34. The method of claim 32 wherein the medical device comprises an implantable medical device.

35. The method of claim 32 wherein the medical device comprises at least one of (1) an implantable infusion pump for selectively dispensing a selected drug, (2) an implantable infusion pump for selectively dispensing insulin, (3) an implantable sensor for sensing a selected state of the body, (4) an implantable sensor for sensing glucose level, or (5) an implantable electrode for selectively stimulating a portion of the body of the patient.

36. The method of claim 32 wherein the randomization algorithm is a pseudo-randomization algorithm.

37. The method of claim 36 wherein the pseudo-randomization is obtained by use of a CRC table.

38. The method of claim 37, further comprising preparing an error checking code using the CRC table; and transmitting the error checking code with the message.

39. The method of claim 37 wherein the at least one messages comprises an identifier of the receiver or the transmitter, an op-code, and data, wherein the identifier and op-code are not randomized but the data is randomized.

40. A process of communicating between medical system components, comprising:

providing an ambulatory medical device (MD) for treating or monitoring a selective state of a body of a patient, the ambulatory medical device having an MD electronic control circuitry with at least one MD telemetry system and at least one MD processor;

controlling, with the MD processor, at least part of the operation of the MD telemetry system and of the ambulatory medical device;

providing a communication device (CD) for sending messages to or receiving messages from the MD telemetry system, the communications device having CD electronic control circuitry with at least one CD telemetry system and at least one CD processor, wherein messages sent between the communication device and the medical device comprise a transmission preamble, an op-code for identifying the type of message being transmitted, a data portion, and an error checking code;

controlling, with the CD processor, at least part of the operation of the CD telemetry system and of the communication device; and adding, on a predetermined basis, segments of information to the data portion of the message prior to transmission, by the medical device or the communication device, wherein each segment of information includes at least one bit transition and wherein at least two bits with opposite values are added to the data portion within a number of bits of data to be transmitted.

41. The method of claim 40 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

42. The method of claim 40 wherein the medical device comprises an implantable medical device.

43. The method of claim 40 wherein the medical device comprises at least one of (1) an implantable infusion pump for selectively dispensing a selected drug, (2) an implantable infusion pump for selectively dispensing insulin, (3) an implantable sensor for sensing a selected state of the body, (4) an implantable sensor for sensing glucose level, or (5) an implantable electrode for selectively stimulating a portion of the body of the patient.

* * * * *